US011912705B2

(12) United States Patent
Canal et al.

(10) Patent No.: US 11,912,705 B2
(45) Date of Patent: Feb. 27, 2024

(54) CATHINONE DERIVATIVES, PHARMACEUTICAL FORMULATIONS, AND METHODS

(71) Applicant: The Corporation of Mercer University, Macon, GA (US)

(72) Inventors: Clinton E. Canal, Atlanta, GA (US); Nader Moniri, Atlanta, GA (US); Yiming Chen, Atlanta, GA (US)

(73) Assignee: The Corporation of Mercer University, Macon, GA (US)

( * ) Notice: Subject to any disclaimer, the term of this patent is extended or adjusted under 35 U.S.C. 154(b) by 57 days.

(21) Appl. No.: 17/407,438

(22) Filed: Aug. 20, 2021

(65) Prior Publication Data

US 2022/0056029 A1    Feb. 24, 2022

Related U.S. Application Data

(60) Provisional application No. 63/068,135, filed on Aug. 20, 2020.

(51) Int. Cl.
| | | |
|---|---|---|
| *C07D 471/08* | (2006.01) | |
| *C07D 211/32* | (2006.01) | |
| *C07D 491/18* | (2006.01) | |
| *C07D 471/04* | (2006.01) | |
| *C07D 223/04* | (2006.01) | |

(52) U.S. Cl.
CPC .......... *C07D 471/08* (2013.01); *C07D 211/32* (2013.01); *C07D 223/04* (2013.01); *C07D 471/04* (2013.01); *C07D 491/18* (2013.01)

(58) Field of Classification Search
CPC .. C07D 471/08; C07D 211/32; C07D 223/04; C07D 471/04; C07D 491/18
See application file for complete search history.

(56) References Cited

U.S. PATENT DOCUMENTS

2008/0234315 A1* 9/2008 Busch-Petersen ... C07D 451/02
546/124
2017/0015650 A1* 1/2017 Brown .................... A61P 29/00

OTHER PUBLICATIONS

Bell; Journal of the American Chemical Society 1960, 82, 151-155. https://doi.org/10.1021/ja01486a035 (Year: 1960).*
Chen; Drug Test Anal. 2019, 11, 990-998. https://doi.org/10.1002%2Fdta.2582 (Year: 2019).*
Liu; PNAS 2018, 115, 12046-12050. https://doi.org/10.1073/pnas.1813988115 (Year: 2018).*
Lutz; J. Org. Chem. 1947, 12, 5, 617-703. https://doi.org/10.1021/jo01169a001 (Year: 1947).*
Wolters; ACS Catal. 2016, 6, 4, 2622-2625. https://doi.org/10.1021/acscatal.6b00134 (Year: 2016).*
Lemke; J. Med. Chem. 1976, 19, 1, 122-126. https://doi.org/10.1021/jm00223a021 (Year: 1976).*
Whitesell; Tetrahedron Letters 1984, 25, 2119-2120. https://doi.org/10.1016/S0040-4039(01)81176-X (Year: 1984).*
Broadley; Molecules 2001, 6, 142-193. https://doi.org/10.3390/60300142 (Year: 2001).*
Chen, Y., et al., Structure-Activity Relationship Study of Psychostimulant Synthetic Cathinones Reveals Nanomolar Antagonist Potency of alpha-Pyrrolidinohexiophenone at Human Muscarinic M2 Receptors, ACS Chem Neuroscience, 2020, 11, 960-968.
Baumann, M., et al., Neuropharmacology of Synthetic Cathinones, Intramural Research Program of National Institute on Drug Abuse, 2018, 252, 113-142.
Eshleman, A. J., et al., Structure-Activity Relationships of Substituted Cathinones, with Transporter Binding, Uptake, and Release, The Journal of Pharmacology and Experimental Therapeutics, Oct. 25, 2016, 360(1), 33.
Roberts, A. J., et al., Intravenous cocaine self-administration in a panel of inbred mouse strains differing in acute locomotor sensitivity to cocaine. Psychopharmacology, 2018 235:4, 235(4), 1179-1189.
Myslivecek, J., Two Players in the Field: Hierarchical Model of Interaction between the Dopamine and Acetylcholine Signaling Systems in the Striatum. Biomedicines, 2021, vol. 9, p. 25, 9(1), 25.
Bloem, B. R., et al., Parkinson's disease, Lancet 2021, 397, 2284-2303.
De La Cruz, J., et al., Can pimavanserin help patients with Parkinson disease psychosis?, American Academy of Physician Assistants, Jan. 2019, vol. 32, 44-45.
Metta, V., L, et al., Gastrointestinal dysfunction in Parkinson's disease: molecular pathology and implications of gut microbiome, probiotics, and fecal microbiota transplantation, Journal of Neurology, Apr. 21, 2021.
Krimmer, S. et al., Methyl, Ethyl, Propyl, Butyl: Futile But Not for Water, as the Correlation of Structure and Thermodynamic Signature Shows in a Congeneric Series of Thermolysin Inhibitors, Chemmedchem 2014, 9, 833-846.
Lebois, E. P., et al., Muscarinic receptor subtype distribution in a central nervous system and relevance to aging and Alzheimer's disease, Neuropharmacology 136, 2018, 362-373.
Frazier, E. P., et al., Signal transduction underlying the control of urinary bladder smooth muscle tone by muscarinic receptors and β-adrenoceptors, Naunyn Schmiedebergs Archives Pharmacology, Dec. 4, 2007, vol. 377, 449-462.
Wojcieszak, J., et al., Cytotoxic Activity of Pyrovalerone Derivatives, an Emerging Group of Psychostimulant Deisign Cathinones, Neurotox. Res, 2016, 30, 239-250.

(Continued)

*Primary Examiner* — Daniel R Carcanague
(74) *Attorney, Agent, or Firm* — Eversheds Sutherland (US) LLP

(57) ABSTRACT

Compounds, such as cathinone derivatives, and pharmaceutical formulations that include the compounds. The compounds may have a first selectivity for a first receptor subtype that is at least 10 times greater than a second selectivity for a second receptor subtype from the same class of receptors. Methods of treating patients, which may include administering to a patient a pharmaceutical formulation that includes a compound, such as a cathinone derivative.

42 Claims, 10 Drawing Sheets

(56) References Cited

OTHER PUBLICATIONS

Gordon, R., et al., Autonomic and endocrine control of cardiovascular function, World Journal of Cardiology, Apr. 26, 2015, 7(4), 204-214.

Beck, 0. et al., Toxicity evaluation of α-Pyrrolidinovalerophernone (α-PVP): results from intoxication cases within the STRIDA project, Clinical Toxicology, Jul. 14, 2016, vol. 54, No. 7, 568-575.

* cited by examiner

CATHINONE DERIVATIVES, PHARMACEUTICAL FORMULATIONS, AND METHODS

CROSS REFERENCE TO RELATED APPLICATIONS

This application claims the priority benefit of U.S. Provisional Patent Application No. 63/068,135 filed Aug. 20, 2020, which is incorporated herein by reference.

BACKGROUND

A number of disorders are affected by the activity of muscarinic acetylcholine receptors (mAChRs or MRs), such as pulmonary, cardiovascular, gastrointestinal, excretion, and neuropsychiatric disorders.

Although mAChRs are targets of many FDA-approved drugs for a number of disorders, these drugs generally lack selectivity at distinct mAChRs, and, as a result, can cause a number of side effects.

There are five closely-related mAChRs expressed in the human body. These receptors are commonly referred to as the M1, M2, M3, M4, and M5 receptors. The close structural relationship among these mAChRs has made the design of mAChR compounds that can selectively target individual mAChRs a significant challenge. For example, there are no highly-selective M2 or M3 receptor antagonists.

Currently, there are no highly sub-type selective mAChR medications on the market. For example, the mAChR antagonist drug atropine is clinically approved for more than 11 disorders, but can cause a number of side effects due to its non-selective activity at each of the mAChRs. The side effects of atropine can include heat prostration, xerostomia, altered taste perception, nausea, vomiting, dysphagia, heartburn, constipation, bloated feeling, paralytic ileus, gastroesophageal reflux, urinary hesitancy and retention, impotence, blurred vision, mydriasis, photophobia, cyclopegia, increased intraocular pressure, heart palpitations, bradycardia (following low doses), tachycardia (at higher doses), headache, flushing, nervousness, drowsiness, weakness, dizziness, insomnia, fever, mental confusion or excitement, restlessness, tremor, delirium, allergic reactions, including anaphylaxis and uritcaria, suppression of lactation, nasal congestion, decreased sweating, etc. (noted in prescribing information, c.f., https://dailymed.nlm.nih.gov/dailymed/).

There remains a need for compounds, including mAChR antagonist compounds, that can selectively target one or more individual receptor subtypes, such as one of mAChR subtypes M1-M5, and reduce or eliminate side effects, including adverse side effects.

BRIEF SUMMARY

Provided herein are compounds, including cathinone derivatives, that can exhibit improved selectivity at distinct mAChRs, and that retain selectivity at mAChRs over other classes of off-targets. For example, the compounds described herein may exhibit improved (e.g., at least 10-fold) selectivity for one mAChR subtype within a class of receptors.

In one aspect, compounds, including cathinone derivatives, are provided. In some embodiments, the compounds include a compound of formula (I), formula (II), formula (III), or a salt thereof:

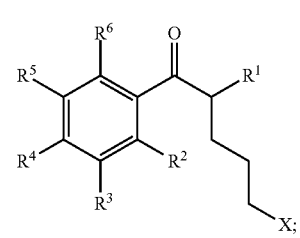

formula (I)

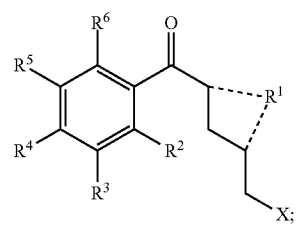

formula (II)

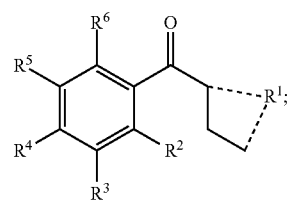

formula (III)

wherein $R^1$ is a $C_1$-$C_{10}$ hydrocarbyl that includes a nitrogen atom, wherein $R^2$, $R^3$, $R^4$, $R^5$, and $R^6$ are independently selected from the group consisting of hydrogen, methyl, methoxy, hydroxy, a first halogen, and a $C_1$-$C_6$ hydrocarbyl comprising a covalent bond between $R^2$ and $R^3$, $R^3$ and $R^4$, $R^4$ and $R^5$, or $R^5$ and $R^6$; and wherein X is selected from the group consisting of hydrogen, methyl, ethyl, hydroxy, and a second halogen. In some embodiments, $R^1$ is not pyrrolidin-1-yl for formula (I).

The compounds described herein may exhibit (i) a first selectivity for a first receptor subtype of a class of receptors, and (ii) one or more second selectivities for one or more second receptor subtypes of the class of receptors, wherein the first selectivity is at least 10 times greater than each of the second selectivities.

In another aspect, pharmaceutical formulations are provided. The pharmaceutical formulations may include any one or more of the compounds described herein. The pharmaceutical formulations may include a pharmaceutically acceptable excipient.

In yet another aspect, methods of treating a patient are provided. In some embodiments, the methods include administering to the patient a pharmaceutical formulation described herein. The patient may have a disorder linked to acetylcholine binding, such as to muscarinic acetylcholine receptor. The administering of the pharmaceutical formulation to the patient may include administering the pharmaceutical formulation orally, intravenously, or topically.

DETAILED DESCRIPTION

Figure 1A:
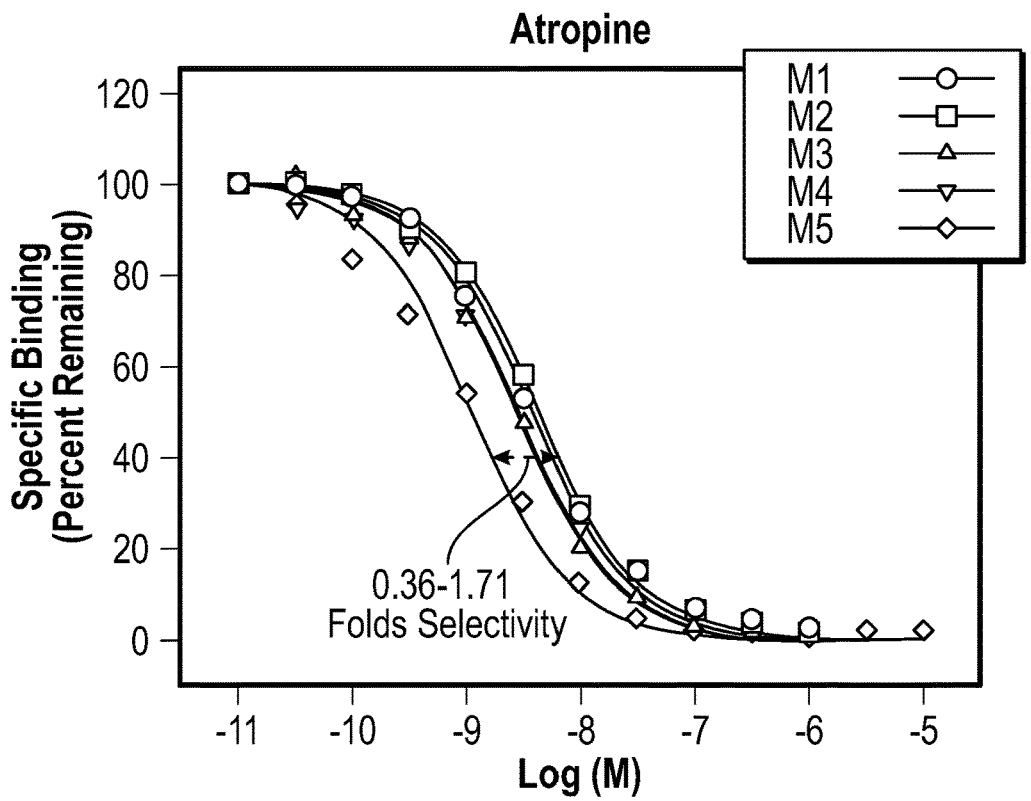
FIG. 1A depicts specific binding data for atropine.

Provided herein are compounds or salts thereof. The salts may include pharmaceutically acceptable salts. In some embodiments, the compounds or salts thereof provided herein are of formula (I), formula (II), or formula (III):

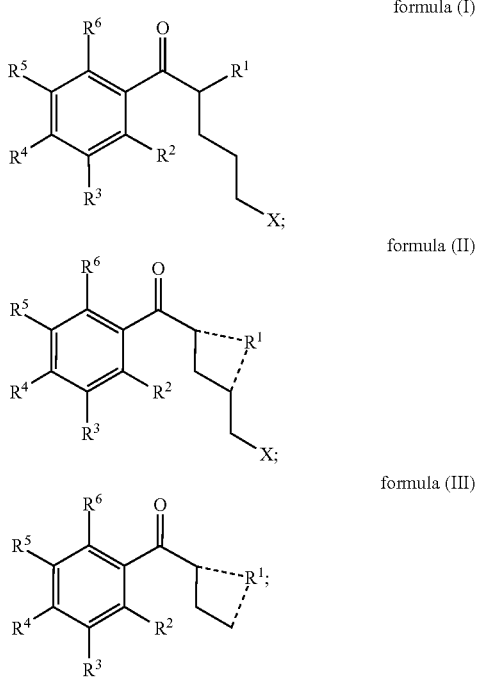

formula (I)

formula (II)

formula (III)

wherein $R^1$ is a $C_1$-$C_{10}$ hydrocarbyl comprising a nitrogen atom; wherein $R^2$, $R^3$, $R^4$, $R^5$, and $R^6$ are independently selected from the group consisting of hydrogen, methyl, methoxy, hydroxy, a first halogen, and a $C_1$-$C_6$ hydrocarbyl comprising a covalent bond between $R^2$ and $R^3$, $R^3$ and $R^4$, $R^4$ and $R^5$, or $R^5$ and $R^6$; and wherein X is selected from the group consisting of hydrogen, methyl, ethyl, hydroxy, and a second halogen. The first halogen and the second halogen, when present, may be the same or different. The first halogen and the second halogen may be selected independently from F, Cl, Br, or I. The nitrogen atom of the $C_1$-$C_{10}$ hydrocarbyl may be a nitrogen heteroatom. The dotted bond lines in formula (II) and formula (III) indicate that the bonds may be bonded to (i) one atom of $R^1$, or (ii) two different atoms of $R^1$. In some embodiments, $R^1$ is not pyrrolidin-1-yl for formula (I).

As used herein, the phrase "$C_1$-$C_6$ hydrocarbyl comprising a covalent bond between $R^2$ and $R^3$, $R^3$ and $R^4$, $R^4$ and $R^5$, or $R^5$ and $R^6$" refers to a $C_1$-$C_6$ hydrocarbyl formed when $R^2$ and $R^3$, $R^3$ and $R^4$, $R^4$ and $R^5$, or $R^5$ and $R^6$ are covalently bonded together. In some embodiments, the $C_1$-$C_6$ hydrocarbyl including a covalent bond between $R^2$ and $R^3$, $R^3$ and $R^4$, $R^4$ and $R^5$, or $R^5$ and $R^6$ also includes at least one heteroatom, such as oxygen. For example, the $C_1$-$C_6$ hydrocarbyl may include one oxygen atom, or two oxygen atoms. Non-limiting examples of the "$C_1$-$C_6$ hydrocarbyl comprising a covalent bond between $R^2$ and $R^3$, $R^3$ and $R^4$, $R^4$ and $R^5$, or $R^5$ and $R^6$" include those depicted below: (i) a $C_3$ hydrocarbyl that includes a covalent bond between $R^4$ and $R^5$, (ii) a $C_2$ hydrocarbyl that includes one oxygen heteroatom and a covalent bond between $R^4$ and $R^5$, and (iii) $C_1$ hydrocarbyl that includes two oxygen heteroatoms and a covalent bond between $R^4$ and $R^5$, but other $C_1$-$C_6$ hydrocarbyls are envisioned:

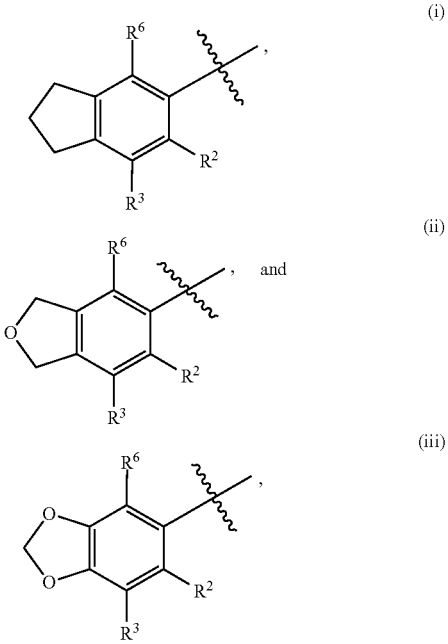

In some embodiments, $R^2$, $R^3$, $R^4$, $R^5$, and $R^6$ are hydrogen, and the compounds or salts thereof are of formula (Ia), formula (IIa), or formula (IIIa):

formula (Ia)

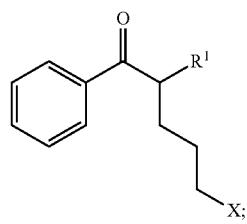

formula (IIa)

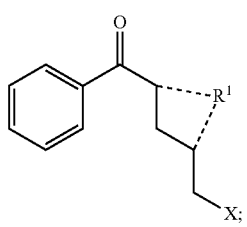

formula (IIIa)

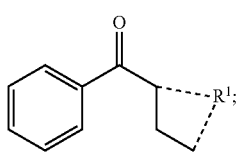

wherein $R^1$ is a $C_1$-$C_{10}$ hydrocarbyl comprising a nitrogen atom; and wherein X is selected from the group consisting of hydrogen, methyl, ethyl, hydroxy, and a second halogen.

In some embodiments, X is methyl, and the compounds and salts thereof are of formula (Ib) or formula (IIb):

formula (Ib)

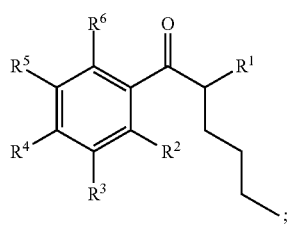

formula (IIb)

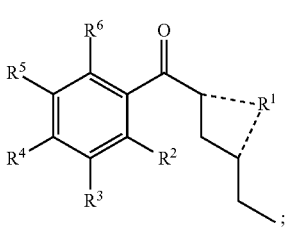

wherein $R^1$ is a $C_1$-$C_{10}$ hydrocarbyl comprising a nitrogen atom; and wherein $R^2$, $R^3$, $R^4$, $R^5$, and $R^6$ are independently selected from the group consisting of hydrogen, methyl, methoxy, hydroxy, a first halogen, and a $C_1$-$C_6$ hydrocarbyl comprising a covalent bond between $R^2$ and $R^3$, $R^3$ and $R^4$, $R^4$ and $R^5$, or $R^5$ and $R^6$.

In some embodiments, X is hydroxy, and the compounds and salts thereof are of formula (Ic) or formula (IIc):

formula (Ic)

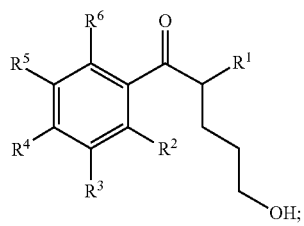

formula (IIc)

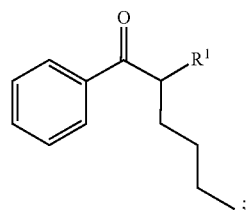

wherein $R^1$ is a $C_1$-$C_{10}$ hydrocarbyl comprising a nitrogen atom; and wherein $R^2$, $R^3$, $R^4$, $R^5$, and $R^6$ are independently selected from the group consisting of hydrogen, methyl, methoxy, hydroxy, a first halogen, and a $C_1$-$C_6$ hydrocarbyl comprising a covalent bond between $R^2$ and $R^3$, $R^3$ and $R^4$, $R^4$ and $R^5$, or $R^5$ and $R^6$.

In some embodiments, $R^2$, $R^3$, $R^4$, $R^5$, and $R^6$ are hydrogen, X is methyl, and the compounds or salts thereof are of formula (Id) or formula (IId):

formula (Id)

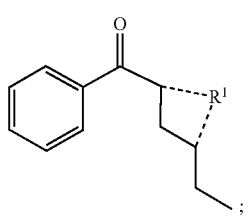

formula (IId)

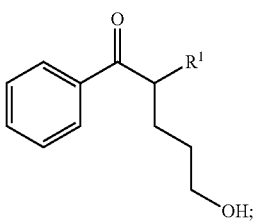

wherein $R^1$ is a $C_1$-$C_{10}$ hydrocarbyl comprising a nitrogen atom.

In some embodiments, $R^2$, $R^3$, $R^4$, $R^5$, and $R^6$ are hydrogen, X is hydroxy, and the compounds or salts thereof are of formula (Ie) or formula (IIe):

formula (Ie)

formula (IIe)

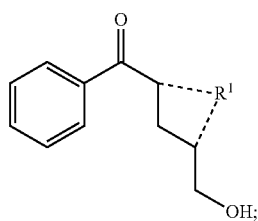

wherein R¹ is a $C_1$-$C_{10}$ hydrocarbyl comprising a nitrogen atom.

In some embodiments, X is ethyl, and the compounds and salts thereof are of formula (IIf):

formula (IIf)

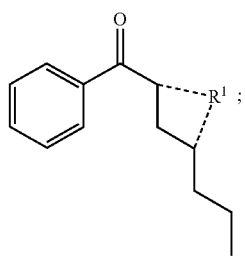

wherein R¹ is a $C_1$-$C_{10}$ hydrocarbyl comprising a nitrogen atom; and wherein R², R³, R⁴, R⁵, and R⁶ are independently selected from the group consisting of hydrogen, methyl, methoxy, hydroxy, a first halogen, and a $C_1$-$C_6$ hydrocarbyl comprising a covalent bond between R² and R³, R³ and R⁴, R⁴ and R⁵, or R⁵ and R⁶.

In some embodiments, R¹ is a $C_1$-$C_{10}$ hydrocarbyl that includes a nitrogen atom, such as a nitrogen heteroatom. R¹ may include one nitrogen atom, or more than one nitrogen atom (e.g., 2, 3, 4 nitrogen atoms, etc.). The nitrogen atom(s) of R¹ may include a primary (1°) nitrogen atom, a secondary (2°) nitrogen atom, a tertiary (3°) nitrogen atom, a quaternary (4°) nitrogen atom, or any combination thereof. In some embodiments, R¹ includes only one nitrogen atom, and the one nitrogen atom is a tertiary nitrogen atom or a quaternary nitrogen atom. In some embodiments, R¹ is a bicyclo $C_1$-$C_{10}$ hydrocarbyl that includes one nitrogen atom. In some embodiments, R¹ is an azabicyclo $C_1$-$C_{10}$ hydrocarbyl that includes one nitrogen atom.

In some embodiments, the compounds or salts thereof have a structure according to formula (I), formula (Ia), formula (Ib), formula (Ic), formula (Id), or formula (Ie), wherein R¹ is an 8-methyl-8-azabicyclo[3.2.1]octanyl. Any atom of the 8-methyl-8-azabicyclo[3.2.1]octanyl may be bonded to the alpha carbon of formula (I), formula (Ia), formula (Ib), formula (Ic), formula (Id), or formula (Ie). In some embodiments, the 8-methyl-8-azabicyclo[3.2.1]octanyl is 8-methyl-8-azabicyclo[3.2.1]octan-3-yl.

In some embodiments, the compound or salt thereof is a compound of formula (I), wherein (i) R¹ is 8-methyl-8-azabicyclo[3.2.1]octan-3-yl, (ii) R², R³, R⁴, R⁵, and R⁶ are hydrogen, (iii) X is methyl, and the compound is 2-(8-methyl-8-azabicyclo[3.2.1]octan-3-yl)-1-phenylhexan-1-one:

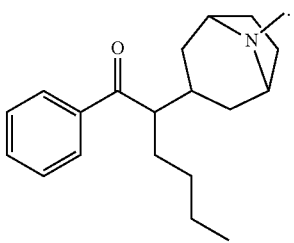 [SMILES: CCCCC(C(=O)c1ccccc1)C1CC2CCC(C1)N2C]

In some embodiments, the compound or salt thereof is a compound of formula (I), wherein (i) R¹ is 8-methyl-8-azabicyclo[3.2.1]octan-3-yl, (ii) R², R³, R⁴, R⁵, and R⁶ are hydrogen, (iii) X is hydroxy, and the compound is 5-hydroxy-2-(8-methyl-8-azabicyclo[3.2.1]octan-3-yl)-1-phenylpentan-1-one:

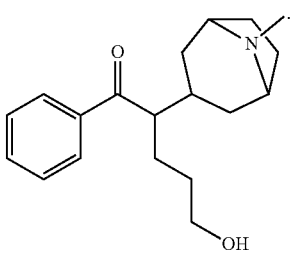 [SMILES: CN1C2CCC1CC(C(CCCO)C(=O)c1ccccc1)C2]

In some embodiments, the compounds or salts thereof have a structure according to formula (I), formula (Ia), formula (Ib), formula (Ic), formula (Id), or formula (Ie), wherein R¹ is an 8,8-dimethyl-8$\lambda^4$-azabicyclo[3.2.1]octanyl. Any atom of the 8,8-dimethyl-8$\lambda^4$-azabicyclo[3.2.1]octanyl may be bonded to the alpha carbon of formula (I), formula (Ia), formula (Ib), formula (Ic), formula (Id), or formula (Ie).

In some embodiments, the compounds or salts thereof have a structure according to formula (I), formula (Ia), formula (Ib), formula (Ic), formula (Id), or formula (Ie), wherein R¹ is a 9-methyl-3-oxa-9-azatricyclo[3.3.1.0$^{2,4}$]nonanyl. Any atom of the 9-methyl-3-oxa-9-azatricyclo[3.3.1.0$^{2,4}$]nonanyl may be bonded to the alpha carbon of formula (I), formula (Ia), formula (Ib), formula (Ic), formula (Id), or formula (Ie).

In some embodiments, the compounds or salts thereof have a structure according to formula (I), formula (Ia), formula (Ib), formula (Ic), formula (Id), or formula (Ie), wherein R¹ is a 9,9-dimethyl-3-oxa-9$\lambda^4$-azatricyclo[3.3.1.0$^{2,4}$]nonanyl. Any atom of the 9,9-dimethyl-3-oxa-9$\lambda^4$-azatricyclo[3.3.1.0$^{2,4}$]nonanyl may be bonded to the alpha carbon of formula (I), formula (Ia), formula (Ib), formula (Ic), formula (Id), or formula (Ie).

In some embodiments, the compounds or salts thereof have a structure according to formula (I), formula (Ia), formula (Ib), formula (Ic), formula (Id), or formula (Ie), wherein R¹ is a N,6-dimethyl-8-oxabicyclo[5.1.0]octan-2-amine. Any atom of the N,6-dimethyl-8-oxabicyclo[5.1.0]octan-2-amine may be bonded to the alpha carbon of formula (I), formula (Ia), formula (Ib), formula (Ic), formula (Id), or formula (Ie). In some embodiments, the compounds or salts thereof have a structure of the formula 2-(2-methyl-6-(methylamino)-8-oxabicyclo[5.1.0]octan-4-yl)-1-phenylhexan-1-one:

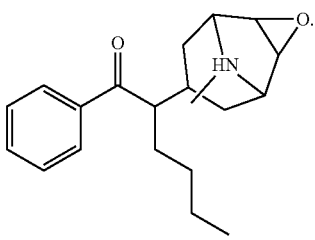 [SMILES: CCCCC(C(=O)c1ccccc1)C1CC2C3OC3C(C1)N2C]

In some embodiments, the compounds or salts thereof have a structure of the formula 5-hydroxy-2-(2-methyl-6-(methylamino)-8-oxabicyclo[5.1.0]octan-4-yl)-1-phenyl-pentan-1-one:

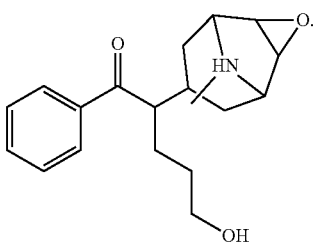 [SMILES: CN1C2CC(C(CCCO)C(=O)c3ccccc3)CC1C1OC12]

In some embodiments, the compounds or salts thereof have a structure according to formula (I), formula (Ia), formula (Ib), formula (Ic), formula (Id), or formula (Ie), wherein $R^1$ is an unsubstituted or substituted piperidinyl. Any atom of the unsubstituted or substituted piperidinyl may be bonded to the alpha carbon of formula (I), formula (Ia), formula (Ib), formula (Ic), formula (Id), or formula (Ie). In some embodiments, the substituted piperidinyl is a 1-methyl piperidinyl, such as 1-methyl piperidin-2-yl, 1-methyl piperidin-3-yl, or 1-methyl piperidin-4-yl.

In some embodiments, the compound or salt thereof is a compound of formula (I), wherein (i) $R^1$ is an unsubstituted piperidin-1-yl, (ii) $R^2$, $R^3$, $R^4$, $R^5$, and $R^6$ are hydrogen, (iii) X is methyl, and the compound is 1-phenyl-2-(piperidin-1-yl)hexan-1-one:

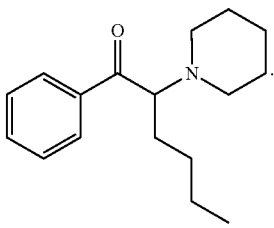 [SMILES: CCCCC(C(=O)c1ccccc1)N1CCCCC1]

In some embodiments, the compound or salt thereof is a compound of formula (I), wherein (i) $R^1$ is an unsubstituted piperidin-1-yl, (ii) $R^2$, $R^3$, $R^4$, $R^5$, and $R^6$ are hydrogen, (iii) X is hydroxy, and the compound is 5-hydroxy-1-phenyl-2-(piperidin-1-yl)pentan-1-one:

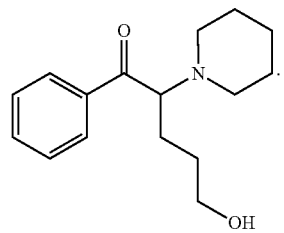 [SMILES: O=C(c1ccccc1)C(CCCO)N1CCCCC1]

In some embodiments, the compound or salt thereof is of formula (I), wherein (i) $R^1$ is 1-methylpiperidin-2-yl, (ii) $R^2$, $R^3$, $R^4$, $R^5$, and $R^6$ are hydrogen, (iii) X is methyl, and the compound is 2-(1-methylpiperidin-2-yl)-1-phenylhexan-1-one:

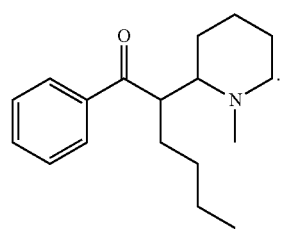 [SMILES: CCCCC(C(=O)c1ccccc1)C1CCCCN1C]

In some embodiments, the compound or salt thereof is of formula (I), wherein (i) $R^1$ is 1-methylpiperidin-2-yl, (ii) $R^2$, $R^3$, $R^4$, $R^5$, and $R^6$ are hydrogen, (iii) X is hydroxy, and the compound is 5-hydroxy-2-(1-methylpiperidin-2-yl)-1-phenylpentan-1-one:

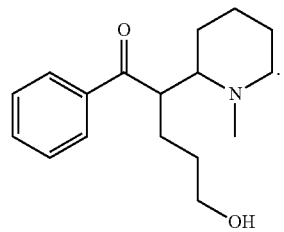 [SMILES: CN1CCCCC1C(CCCO)C(=O)c1ccccc1]

In some embodiments, the compounds or salts thereof have a structure according to formula (I), formula (Ia), formula (Ib), formula (Ic), formula (Id), or formula (Ie), wherein $R^1$ is an unsubstituted or substituted azepanyl. Any atom of the unsubstituted or substituted azepanyl may be bonded to the alpha carbon of formula (I), formula (Ia), formula (Ib), formula (Ic), formula (Id), or formula (Ie). In some embodiments, the substituted azepanyl is a 1-methyl azepanyl, such as 1-methyl azepan-2-yl, 1-methyl azepan-3-yl, or 1-methyl azepan-4-yl.

In some embodiments, the compounds or salts thereof have a structure according to formula (I), wherein (i) $R^1$ is azepan-1-yl, (ii) $R^2$, $R^3$, $R^4$, $R^5$, and $R^6$ are hydrogen, (iii) X is methyl, and the compound is 2-(azepan-1-yl)-1-phenyl-hexan-1-one:

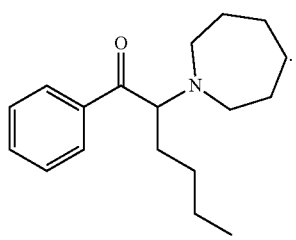 [SMILES: CCCCC(C(=O)c1ccccc1)N1CCCCCC1]

In some embodiments, the compounds or salts thereof are of formula (I), wherein (i) $R^1$ is azepan-1-yl, (ii) $R^2$, $R^3$, $R^4$, $R^5$, and $R^6$ are hydrogen, (iii) X is hydroxy, and the compound is 2-(azepan-1-yl)-5-hydroxy-1-phenylpentan-1-one:

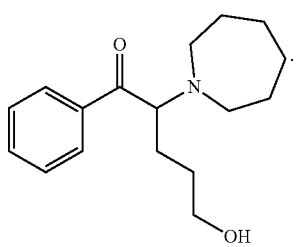 [SMILES: O=C(c1ccccc1)C(CCCO)N1CCCCCC1]

In some embodiments, the compounds or salts thereof have a structure according to formula (I), formula (Ia), formula (Ib), formula (Ic), formula (Id), or formula (Ie), wherein $R_1$ is an unsubstituted or substituted pyrrolidinyl. Any atom of the pyrrolidinyl may be bonded to the alpha carbon of formula (I), formula (Ia), formula (Ib), formula (Ic), formula (Id), or formula (Ie). In some embodiments, the structures of formula (I) do not include an unsubstituted or substituted pyrrolidinyl at $R^1$.

In some embodiments, the compounds or salts thereof have a structure according to formula (I), formula (Ia), formula (Ib), formula (Ic), formula (Id), or formula (Ie), wherein $R^1$ is an unsubstituted or substituted azocanyl. Any atom of the unsubstituted or substituted azocanyl may be bonded to the alpha carbon of formula (I), formula (Ia), formula (Ib), formula (Ic), formula (Id), or formula (Ie). In some embodiments, the substituted azocanyl is a 1-methyl azocanyl, such as 1-methyl azocan-2-yl, 1-methyl azocan-3-yl, or 1-methyl azocan-4-yl.

In some embodiments, the compounds or salts thereof have a structure according to formula (II), formula (IIa), formula (IIb), formula (IIc), formula (IId), formula (IIe), or formula (IIf), wherein $R^1$ is a hydrocarbyl that imparts formula (II), formula (IIa), formula (IIb), formula (IIc), formula (IId), formula (IIe), or formula (IIf) with a structure selected from the group consisting of—

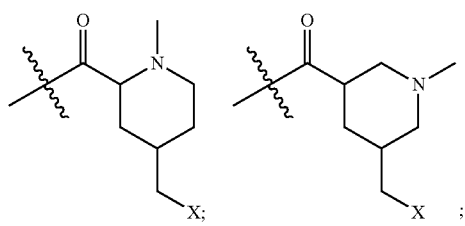

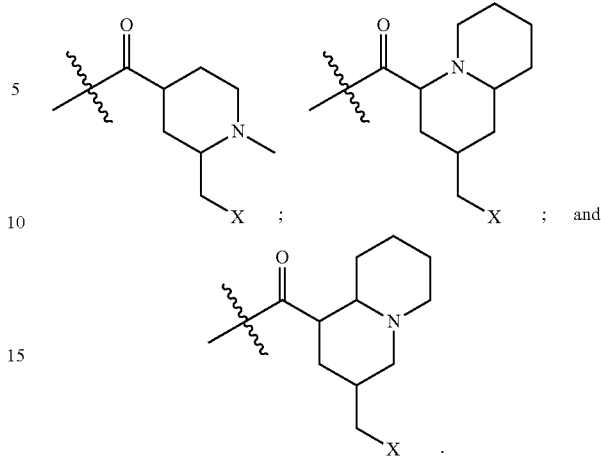

Other structures are envisioned, however, such as substituted derivatives of the foregoing structures.

In some embodiments, the compounds or salts thereof have a structure according to formula (III) or formula (IIIa), wherein $R^1$ is a hydrocarbyl that imparts formula (III) with a structure selected from the group consisting of—

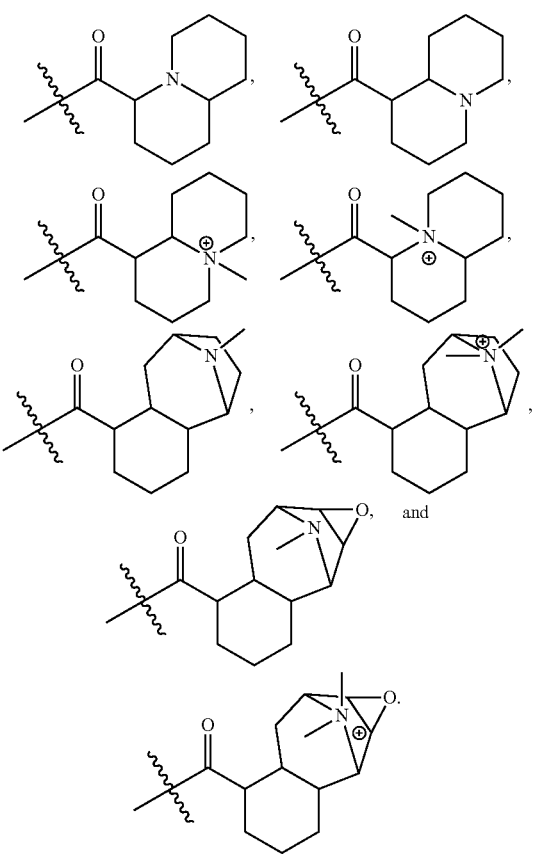

Other embodiments are envisioned, however, including substituted derivatives of the foregoing.

In some embodiments, the compound of formula (I) or formula (II) is selected from the group consisting of—

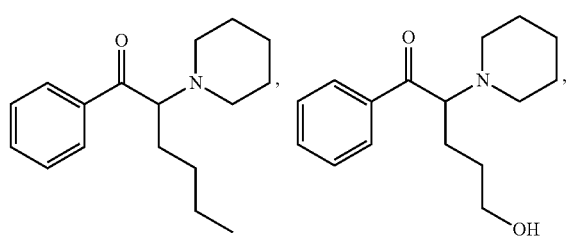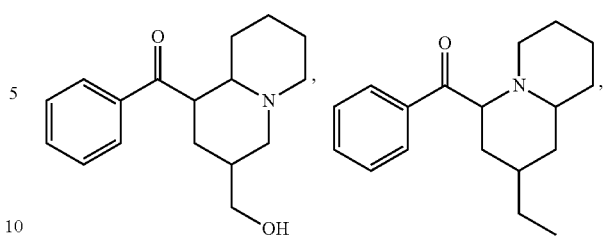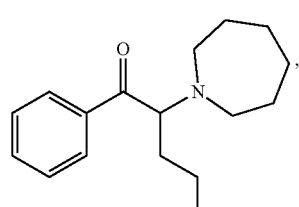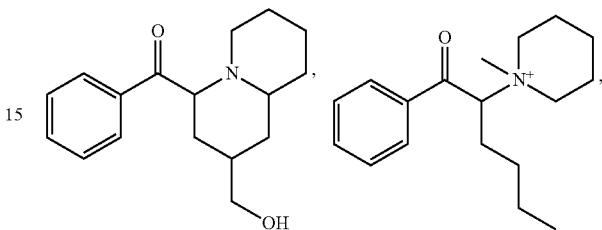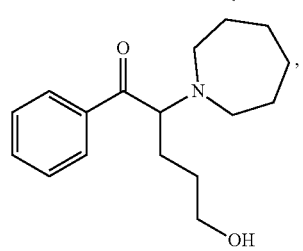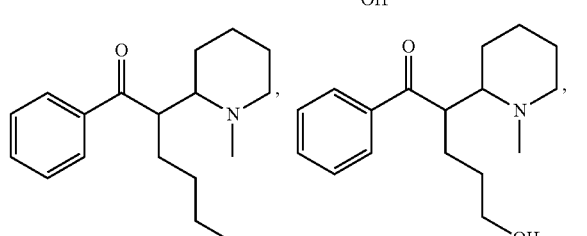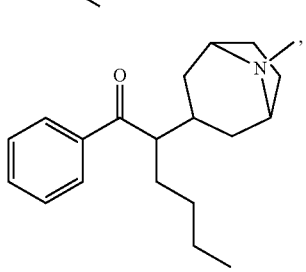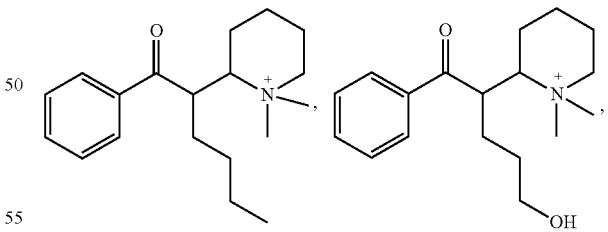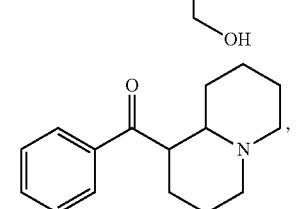

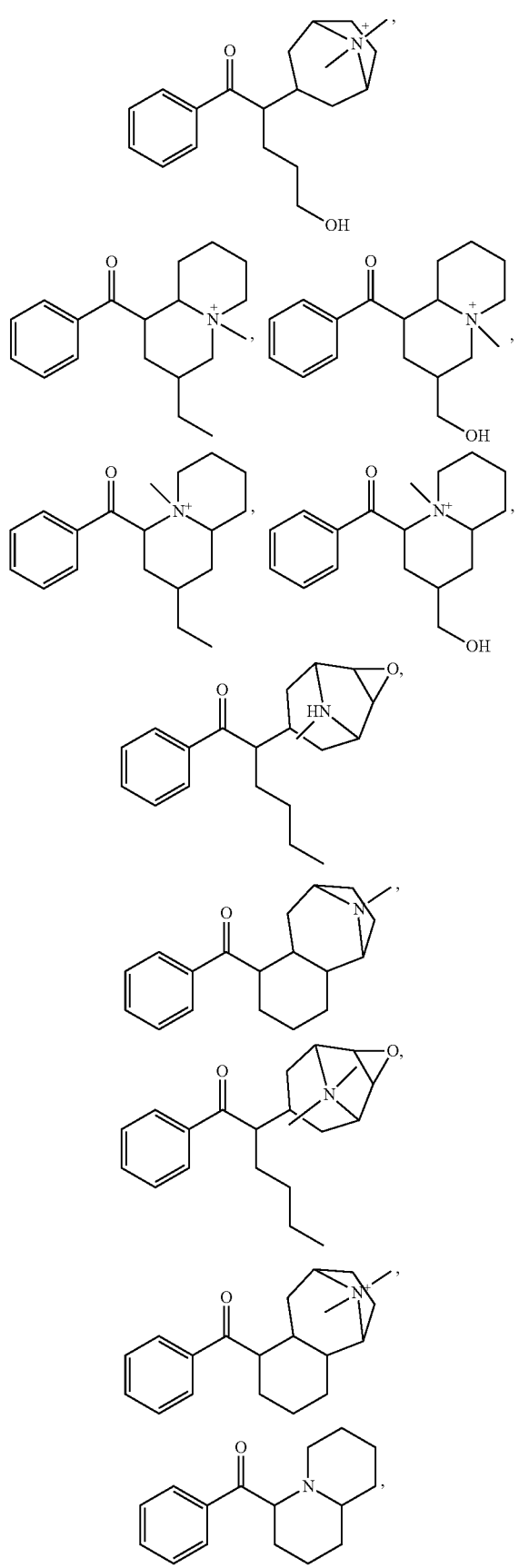

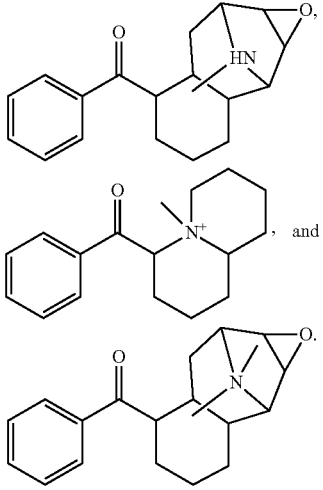

The foregoing compounds that include a cation may include any counteranion, such as a pharmaceutically acceptable counteranion.

In some embodiments, the compounds or salts thereof have a structure according to formula (I), formula (Ia), formula (Ib), formula (Ic), formula (Id), or formula (Ie), wherein the compound exhibits a first selectivity for a first receptor subtype of a class of receptors, one or more second selectivities for one or more second receptor subtypes of the class of receptors, and the first selectivity is at least 10 times greater than each of the one or more second selectivities. For example, if there are five receptor subtypes—A, B, C, D, and E—and a compound of formula (I) exhibits the following arbitrary selectivities for the five receptor subtypes—20, 1.9, 1.8, 1.7, and 1.5, respectively—then, in this example, the first selectivity is 20, and the second selectivities are 1.9, 1.8, 1.7, and 1.5.

In some embodiments, the first selectivity is about 10 times to about 1000 times greater than the one or more second selectivities. In some embodiments, the first selectivity is about 10 times to about 750 times greater than the one or more second selectivities. In some embodiments, the first selectivity is about 10 times to about 500 times greater than the one or more second selectivities. In some embodiments, the first selectivity is about 10 times to about 250 times greater than the one or more second selectivities. In some embodiments, the first selectivity is about 10 times to about 100 times greater than the one or more second selectivities. In some embodiments, the first selectivity is about 10 times to about 90 times greater than the one or more second selectivities. In some embodiments, the first selectivity is about 10 times to about 80 times greater than the one or more second selectivities. In some embodiments, the first selectivity is about 10 times to about 70 times greater than the one or more second selectivities. In some embodiments, the first selectivity is about 10 times to about 60 times greater than the one or more second selectivities. In some embodiments, the first selectivity is about 10 times to about 50 times greater than the one or more second selectivities. In some embodiments, the first selectivity is about 10 times to about 40 times greater than the one or more second selectivities. In some embodiments, the first selectivity is about 10 times to about 30 times greater than the one or more second selectivities. In some embodiments, the first selectivity is about 10 times to about 20 times greater than the one or more second selectivities.

In some embodiments, the class of receptors includes acetylcholine receptors. In some embodiments, the class of receptors includes the muscarinic acetylcholine receptors (mAChRs), which may include the following receptor subtypes: M1, M2, M3, M4, or M5. In some embodiments, (i) the first receptor subtype is M2, and the one or more second receptor subtypes include M1, M3, M4, and M5, (ii) the first receptor subtype is M1, and the one or more second receptor subtypes include M2, M3, M4, and M5, (iii) the first receptor subtype is M3, and the one or more second receptor subtypes include M1, M2, M4, and M5, (iv) the first receptor subtype is M4, and the one or more second receptor subtypes include M1, M2, M3, and M5, and (v) the first receptor subtype is M5, and the one or more second receptor subtypes include M1, M2, M3, and M4.

In addition to these mAChRs, in some embodiments, the class of receptors includes monoamine transporters, which may include the monoamine transporters: DAT, NET, and/or SERT. In some embodiments, (i) the first receptor is the dopamine transporter (DAT), and one or more second receptors include NET and SERT, (ii) the first receptor is the norepinephrine transporter (NET), and the one or more second receptors include DAT and SERT, and/or (iii) the first receptor is the serotonin transporter (SERT), and the one or more second receptors include DAT and NET. In addition to the foregoing, in some embodiments, the class of receptors includes the histamine receptors, the serotonin receptors, the dopamine receptors, the norepinephrine receptors, and all other G protein-coupled receptors (GPCRs).

In some embodiments, the compounds described herein exhibit muscarinic receptor subtype selectivity (e.g., ≥10-fold) and muscarinic selectivity (e.g., ≥10-fold) over one or more other classes of proteins (i.e., "off-targets"). Non-limiting examples of off-targets include monoamine transporters and GPCRs. Non-limiting examples of monoamine transporters include DAT, NET, and/or SERT. Non-limiting examples of GPCRs include histamine receptors, such as H1, and serotonin receptors, such as 5-HT2B.

In some embodiments, the compounds described herein exhibit a first selectivity for a first receptor subtype of a first class of receptors, one or more second selectivities for (i) one or more second receptor subtypes of the first class of receptors and (ii) one or more receptor subtypes of a second class of receptors, and the first selectivity is at least 10 times greater than each of the one or more second selectivities. In some embodiments, the first class of receptors includes acetylcholine receptors. In some embodiments, the first class of receptors includes the muscarinic acetylcholine receptors (mAChRs), which may include the following receptor subtypes: M1, M2, M3, M4, or M5. The second class of receptors may be selected from the group consisting of one or more monoamine transporters, one or more GPCRs, and a combination thereof. The one or more monoamine transporters may be selected from the group consisting of DAT, NET, SERT, and a combination thereof. The one or more GPCRs may include a histamine receptor, such as H1.

Pharmaceutical Formulations

Provided herein are pharmaceutical formulations that include at least one compound of formula (I) described herein.

The pharmaceutical formulations may consist only of a compound of formula (I) as described herein. One or more pharmaceutically acceptable excipients may be included in the pharmaceutical formulations. The pharmaceutical formulations may include a therapeutically effective amount of a compound of formula (I). A "therapeutically effective" amount is an amount effective to achieve a desired treatment, which may include eliminating one or more symptoms, lessening one or more symptoms, preventing one or more symptoms from worsening, prophylaxis, or a combination thereof.

A compound of formula (I) that is present in a pharmaceutical formulation may include a compound of a specific formula described herein and/or its alternative forms, such as salt forms, free acid forms, free base forms, and hydrates.

Pharmaceutically acceptable excipients are known in the art and may include lubricants, viscosity modifiers, surface active agents, osmotic agents, diluents, and other non-active ingredients of the formulation intended to facilitate handling, stability, dispersibility, wettability, and/or release kinetics of a compound of formula (I).

The pharmaceutical formulations described herein may be in any physical form. In some embodiments, the pharmaceutical formulations are in a solid or semi-solid form. The solid form may be, for example, a tablet. The semi-solid form may be, for example, an emulsion, a suspension, a gel, or a paste. In some embodiments, the pharmaceutical formulations include no or a minimum quantity of excipient for the same reasons of volume/size minimization.

The pharmaceutical formulations may be configured for any mode of administration. In some embodiments, the pharmaceutical formulations are configured to be administered orally, intravenously, topically, etc.

The pharmaceutical formulations and/or compounds described herein can be used to treat a number of disorders of the autonomic and central nervous systems, including, but not limited to, disorders affected by the activity at acetylcholine receptors, such as the mAChRs. The disorders, therefore, may include disorders of the autonomic nervous system. These disorders may include urinary system disorders (e.g., overactive bladder), gastrointestinal disorders (e.g., constipation or irritable bowel syndrome), cardiovascular disorders (e.g., bradycardia), pulmonary disorders (e.g., chronic obstructive pulmonary disease (COPD)), other autonomic nervous system disorders (e.g., excessive sweating), etc. Owing to their distribution in the central nervous system, the disorders, therefore, may include disorders of the brain. These disorders may include neurological disorders (e.g., fragile X syndrome, autism spectrum disorder, Parkinson's disease, Huntington's disease, Alzheimer's disease and other dementias, e.g. Lewy body dementia, and additionally, non-neurological symptoms associated with them, e.g., gastrointestinal dysfunction in Parkinson's disease or fragile X syndrome or autism spectrum disorder, irritability in fragile X syndrome or autism spectrum disorder) and neuropsychiatric disorders (e.g., psychoses (e.g., schizophrenia), major depression, anxiety disorders (e.g., generalized anxiety, social anxiety, obsessive compulsive disorder, etc.), sexual dysfunction, and substance use disorders (e.g., opioid use disorder, alcohol use disorder, psychostimulant (cocaine, methamphetamine, amphetamine) use disorder and nicotine use disorder).

Methods of Treating a Patient

Also provided herein are methods of treating a patient. In some embodiments, the methods include administering to a patient a pharmaceutical formulation as described herein.

A patient treated by the methods described herein may or may not have a disorder. In some embodiments, a patient has a disorder linked to acetylcholine receptor binding, such as muscarinic acetylcholine receptor binding.

In some embodiments, the administering to a patient includes administering the pharmaceutical formulation orally, intravenously, or topically.

The phrases "$C_1$-$C_{10}$ hydrocarbyl comprising a nitrogen atom," and the like, as used herein, generally refer to aliphatic, aryl, or arylalkyl groups containing 1 to 10 carbon atoms and at least one nitrogen atom bonded to at least one of the 1 to 10 carbon atoms. The phrases "$C_1$-$C_6$ hydrocarbyl" and the like, as used herein, generally refer to aliphatic, aryl, or arylalkyl groups containing 1 to 6 carbon atoms and, optionally, at least one heteroatom bonded to at least one of the 1 to 6 carbon atoms. Examples of aliphatic groups, in each instance, include, but are not limited to, an alkyl group, a cycloalkyl group, an alkenyl group, a cycloalkenyl group, an alkynyl group, an alkadienyl group, a cyclic group (e.g., a bicyclic group), and the like, and includes all substituted, unsubstituted, branched, and linear analogs or derivatives thereof, in each instance having 1 to about 10 carbon atoms. Examples of alkyl groups include, but are not limited to, methyl, ethyl, propyl, isopropyl, n-butyl, t-butyl, isobutyl, pentyl, hexyl, isohexyl, heptyl, 4,4-dimethylpentyl, octyl, 2,2,4-trimethylpentyl, nonyl, decyl, undecyl and dodecyl. Cycloalkyl moieties may be monocyclic or multicyclic (e.g., bicyclic), and examples include cyclopropyl, cyclobutyl, cyclopentyl, cyclohexyl, cycloheptanyl, and adamantyl. Additional examples of alkyl moieties have linear, branched and/or cyclic portions (e.g., 1-ethyl-4-methyl-cyclohexyl). Representative alkenyl moieties include vinyl, allyl, 1-butenyl, 2-butenyl, isobutylenyl, 1-pentenyl, 2-pentenyl, 3-methyl-1-butenyl, 2-methyl-2-butenyl, 2,3-dimethyl-2-butenyl, 1-hexenyl, 2-hexenyl, 3-hexenyl, 1-heptenyl, 2-heptenyl, 3-heptenyl, 1-octenyl, 2-octenyl, 3-octenyl, 1-nonenyl, 2-nonenyl, 3-nonenyl, 1-decenyl, 2-decenyl and 3-decenyl. Representative alkynyl moieties include acetylenyl, propynyl, 1-butynyl, 2-butynyl, 1-pentynyl, 2-pentynyl, 3-methyl-1-butynyl, 4-pentynyl, 1-hexynyl, 2-hexynyl, 5-hexynyl, 1-heptynyl, 2-heptynyl, 6-heptynyl, 1-octynyl, 2-octynyl, 7-octynyl, 1-nonynyl, 2-nonynyl, 8-nonynyl, 1-decynyl, 2-decynyl and 9-decynyl. Examples of aryl or arylalkyl moieties include, but are not limited to, anthracenyl, azulenyl, biphenyl, fluorenyl, indan, indenyl, naphthyl, phenanthrenyl, phenyl, 1,2,3,4-tetrahydro-naphthalene, tolyl, xylyl, mesityl, benzyl, and the like, including any heteroatom substituted derivative thereof. A heteroatom of a "$C_1$-$C_6$ hydrocarbyl" or a nitrogen atom of a "$C_1$-$C_{10}$ hydrocarbyl comprising a nitrogen atom" may (i) replace a carbon atom of any of the foregoing example moieties, and/or (ii) be bonded to any one or more carbon atoms of the foregoing example moieties.

Unless otherwise indicated, the term "substituted," when used to describe a chemical structure or moiety, refers to a derivative of that structure or moiety wherein one or more of its hydrogen atoms is substituted with a chemical moiety or functional group such as alcohol, alkoxy, alkanoyloxy, alkoxycarbonyl, alkenyl, alkyl (e.g., methyl, ethyl, propyl, t-butyl), alkynyl, alkylcarbonyloxy (—OC(O)alkyl), amide (—C(O)NH-alkyl- or -alkylNHC(O)alkyl), tertiary amine (such as alkylamino, arylamino, arylalkylamino), aryl, aryloxy, azo, carbamoyl (—NHC(O)O-alkyl- or —OC(O)NH-alkyl), carbamyl (e.g., $CONH_2$, as well as CONH-alkyl, CONH-aryl, and CONH-arylalkyl), carboxyl, carboxylic acid, cyano, epoxy, ester, ether (e.g., methoxy, ethoxy), halo, haloalkyl (e.g., —$CCl_3$, —$CF_3$, —$C(CF_3)_3$), heteroalkyl, isocyanate, isothiocyanate, nitrile, nitro, phosphodiester, sulfide, sulfonamido (e.g., $SO_2NH_2$), sulfone, sulfonyl (including alkylsulfonyl, arylsulfonyl and arylalkylsulfonyl), sulfoxide, thiol (e.g., sulfhydryl, thioether) or urea (—NHCONH-alkyl-).

All referenced publications are incorporated herein by reference. Furthermore, where a definition or use of a term in a reference, which is incorporated by reference herein, is inconsistent or contrary to the definition of that term provided herein, the definition of that term provided herein applies and the definition of that term in the reference does not apply.

While certain aspects of conventional technologies have been discussed to facilitate disclosure of various embodiments, applicants in no way disclaim these technical aspects, and it is contemplated that the present disclosure may encompass one or more of the conventional technical aspects discussed herein.

The present disclosure may address one or more of the problems and deficiencies of known methods and processes. However, it is contemplated that various embodiments may prove useful in addressing other problems and deficiencies in a number of technical areas. Therefore, the present disclosure should not necessarily be construed as limited to addressing any of the particular problems or deficiencies discussed herein.

In this specification, where a document, act or item of knowledge is referred to or discussed, this reference or discussion is not an admission that the document, act or item of knowledge or any combination thereof was at the priority date, publicly available, known to the public, part of common general knowledge, or otherwise constitutes prior art under the applicable statutory provisions; or is known to be relevant to an attempt to solve any problem with which this specification is concerned.

In the descriptions provided herein, the terms "includes," "is," "containing," "having," and "comprises" are used in an open-ended fashion, and thus should be interpreted to mean "including, but not limited to." When compounds, formulations, or methods are claimed or described in terms of "comprising" various steps or components, the compounds, formulations, or methods can also "consist essentially of" or "consist of" the various steps or components, unless stated otherwise.

The terms "a," "an," and "the" are intended to include plural alternatives, e.g., at least one. For instance, the disclosure of "a compound," "an excipient," and the like, is meant to encompass one, or mixtures or combinations of more than one compound, excipient, and the like, unless otherwise specified.

Various numerical ranges may be disclosed herein. When Applicant discloses or claims a range of any type, Applicant's intent is to disclose or claim individually each possible number that such a range could reasonably encompass, including end points of the range as well as any sub-ranges and combinations of sub-ranges encompassed therein, unless otherwise specified. Moreover, all numerical end points of ranges disclosed herein are approximate. As a representative example, Applicant discloses, in some embodiments, that a first selectivity is about 10 times to about 20 times greater than one or more second selectivities. This range should be interpreted as encompassing about 10 times and about 20 times, and further encompasses "about" each of 11 times, 12 times, 13 times, 14 times, 15 times, 16 times, 17 times, 18 times, or 19 times, including any ranges and sub-ranges between any of these values.

As used herein, the term "about" means plus or minus 10% of the numerical value of the number with which it is being used.

EXAMPLES

The present invention is further illustrated by the following examples, which are not to be construed in any way as imposing limitations upon the scope thereof. On the contrary, it is to be clearly understood that resort may be had to various other aspects, embodiments, modifications, and equivalents thereof which, after reading the description herein, may suggest themselves to one of ordinary skill in the art without departing from the spirit of the present invention or the scope of the appended claims. Thus, other aspects of this invention will be apparent to those skilled in the art from consideration of the specification and practice of the invention disclosed herein.

Example 1: 2-(2-methyl-6-(methylamino)-8-oxabicyclo[5.1.0]octan-4-yl)-1-phenylpentan-1-one In this example, 2-(2-methyl-6-(methylamino)-8-oxabicyclo[5.1.0]octan-4-yl)-1-phenylpentan-1-one is prepared and used in the methods provided herein. The compound has the following structure:

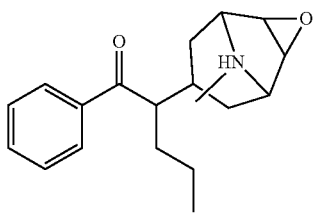 [SMILES: CCCC(C(=O)c1ccccc1)C1CC2C3OC3C(C1)N2C]

Example 2: 2-(8-methyl-8-azabicyclo[3.2.1]octan-3-yl)-1-phenylpentan-1-one

In this example, 2-(8-methyl-8-azabicyclo[3.2.1]octan-3-yl)-1-phenylpentan-1-one is prepared and used in the methods provided herein. The compound has the following structure:

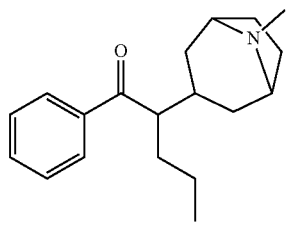 [SMILES: CCCC(C(=O)c1ccccc1)C1CC2CCC(C1)N2C]

Example 3: (8-methyl-2-(methylamino)decahydro-2H-benzo[4,5]cyclohepta[1,2-b]oxiren-6-yl)(phenyl)methanone In this example, (8-methyl-2-(methylamino)decahydro-2H-benzo[4,5]cyclohepta[1,2-b]oxiren-6-yl)methanone is prepared and used in the examples herein. The compound has the following structure:

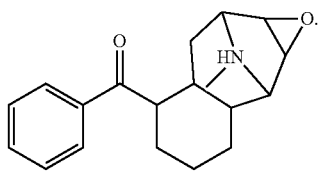 [SMILES: CN1C2CC3C(C(=O)c4ccccc4)CCCC3C1C1OC12]

Example 4: (10-methyldecahydro-1H-5,8-epiminobenzo[7]annulen-1-yl)(phenyl)methanone In this example, (10-methyldecahydro-1H-5,8-epiminobenzo[7]annulen-1-yl)(phenyl)methanone is prepared and used in the examples herein. The compound has the following structure:

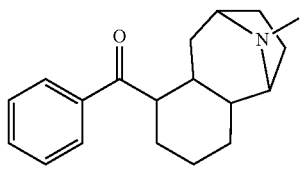 [SMILES: CN1C2CCC1C1CCCC(C(=O)c3ccccc3)C1C2]

Example 5: Synthesis of 1-phenyl-2-(piperidin-1-yl)hexan-1-one and 2-(azepan-1-yl)-1-phenylhexan-1-one In this example, 1-phenyl-2-(piperidin-1-yl)hexan-1-one (1) and 2-(azepan-1-yl)-1-phenylhexan-1-one (2) were synthesized according to the following procedures, which may be modified by a person of ordinary skill in the art to produce other compounds described herein.

Step 1—Synthesis of 1-phenylhexan-1-one

To a stirred solution of benzene (460 mL, 6 eq.) in dichloromethane (DCM) (350 mL) at room temperature, cooled to 0° C., there was slowly added $AlCl_3$ (172 g, 1.5 eq.) at 0° C. over 30 minutes. The reaction mixture was stirred at 0° C. for 30 minutes.

Then there was added by slow dropwise addition, hexanoyl chloride (116 g, 1 eq.), dissolved in 250 mL and cooled to 0° C. The reaction was returned to room temperature and stirred for 1 hour. Reaction progress was monitored by thin layer chromatography (TLC) analysis, which indicated complete consumption of the starting material.

The reaction mixture was quenched with ice and extracted with 2×250 mL DCM, and then washed twice with 500 mL 5% NaOH solution.

The organic layer was dried over anhydrous $Na_2SO_4$, filtered, and evaporated under reduced pressure to obtain a crude compound, distilled at 100° C. at high vacuum, to obtain 1-phenylhexan-1-one (145 g, 95%) as a colorless liquid.

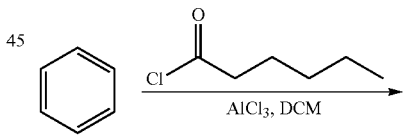

Step 1

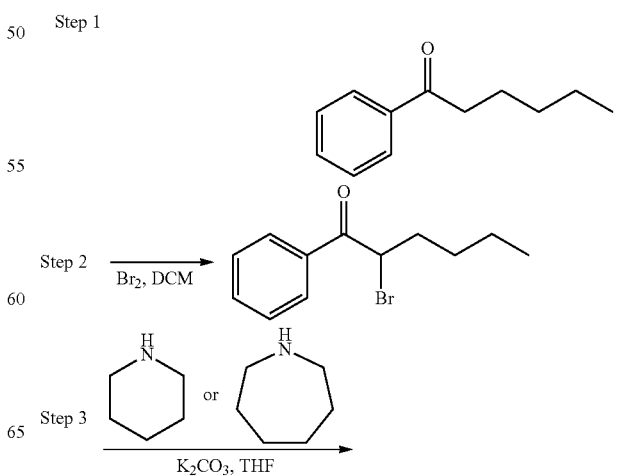

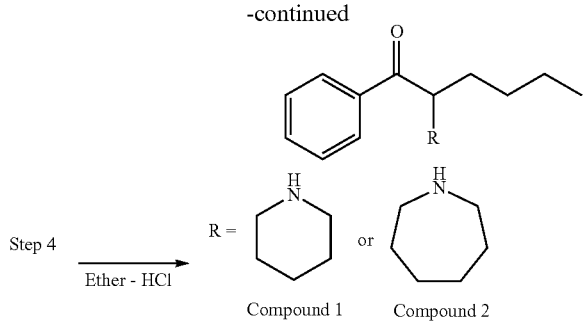

Step 4
Ether - HCl

R = Compound 1 or Compound 2

Step 2—Synthesis of 2-bromo-1-phenylhexanone

A stirred solution of 1-phenylhexan-1-one (20 g, 1 eq.) in 100 mL DCM at room temperature was cooled to 0° C. By slow dropwise addition over a 2 hour period, there was added (18.4 g, 0.9 eq.) bromine, dissolved in 100 mL DCM, and the reaction was kept at 0° C.

The reaction then was allowed to reach room temperature, and then stirred for 30 minutes due to HBr fume generation. Reaction progress was monitored by TLC, which indicated the complete consumption of starting material.

The reaction mixture was quenched with 100 mL of ice-cold water, washed with Hypo (2×100 mL) and 100 mL of a brine solution. The organic layer was dried over anhydrous $Na_2SO_4$, filtered, and evaporated under reduced pressure to obtain 2-bromo-1-phenylhexan-1-one (28 g) as a colorless liquid. The compound was confirmed by $^1$H NMR, and used in the following step without further purification.

Step 3—1-phenyl-2-(piperidin-1-yl)hexan-1-one

A stirred solution at room temperature of 2-bromo-1-pheylhexan-1-one (14 g, crude, 1 eq.) and $K_2CO_3$ (15.6 g, 2 eq.) in 70 mL tetrahydrofuran (THF) was cooled to 0° C., upon which 5.2 g (1.1 eq.) of piperidine was added via slow dropwise addition over 10 minutes. The temperature was monitored and maintained at 0° C. The reaction was allowed to return to room temperature, and was stirred for 16 hours. Reaction progress was monitored by TLC analysis, which indicated the complete consumption of the starting material. The reaction mixture was filtered and washed with 50 mL of ethyl acetate.

The pH was adjusted to 2 using 10 mL of a 2N HCl solution, and washed with 3 portions of 25 mL MTBE. The pH of the aqueous layer was adjusted to 12 with 20 mL of a 2 N NaOH solution and extracted with 3 portions of 50 mL MTBE, and then washed with 50 mL of a brine solution. The organic layer was dried over anhydrous $Na_2SO_4$, filtered, and evaporated under reduced pressure to obtain 1-phenyl-2-(piperidine-1-yl)-hexan-1-one (9.0 g, 65% two steps yield) as a brown colored liquid. The filtrate was evaporated at reduced pressure to obtain a crude compound. The compound was confirmed by $^1$H NMR.

Step 4—Synthesis of 1-phenyl-2-(piperidine-1-yl)hexan-1-one hydrochloride

To a stirred solution of 20 mL diethyl ether, 5 g of 1-phenyl-2-(piperidine-1-yl)hexan-1-one was added at room temperature and then cooled to 0° C. HCl in 10 mL diethyl ether was added to the mixture and stirred for 6 hours at 0° C. The mixture was filtered and dried under a high vacuum to obtain 4.9 g (85.6%) of 1-phenyl-2-(piperidine-1-yl) hexan-1-one hydrochloride as a white solid. The compound was confirmed by $^1$H NMR and HPLC.

Step 5—Synthesis of 2-(azepan-1-yl)-1-phenylhexan-1-one

To a stirred solution of 14 g (crude, 1 eq.) 2-bromo-1-phenylhexan-1-one in 70 mL THF, at room temperature, there was added 15.6 g $K_2CO_3$ (2 eq.). After addition, the reaction was cooled to 0° C. Slowly, dropwise, azepane was added (6.0 g, 1.1 eq.) at 0° C. over 10 minutes. The reaction was allowed to reach room temperature and then stirred for 16 hours.

Reaction progress was monitored by TLC analysis, which indicated complete consumption of starting material.

The reaction mixture was filtered and washed with 50 mL ethyl acetate. The filtrate was evaporated under reduced pressure to obtain a crude compound. The pH was adjusted to 2 using 10 mL of a 2 N HCl solution, and then washed with 3 portions of 25 mL MTBE.

The pH of the aqueous layer was adjusted to 12 with a 20 mL of a 2 N NaOH solution, and extracted with 3 portions of 50 mL MTBE, and then washed with 50 mL of a brine solution. The organic layer was dried over anhydrous $Na_2SO_4$, filtered, and evaporated under reduced pressure to obtain 2-(azepan-1-yl)-1-phenylhexan-1-one (9.5 g, 66% two steps yield) as a brown colored liquid. The compound was confirmed by $^1$H NMR.

Step 6—Synthesis of 2-(azepan-1-yl)-1-phenylhexan-1-one hydrochloride

To a stirred solution at room temperature of 5 g 2-(azepan-1-yl)-1-phenylhexan-1-one in 20 mL diethyl ether, there was added (after cooling to 0° C.) HCl in 10 mL diethyl ether (10 mL) and stirred for 6 hours. The mixture was filtered and dried under a high vacuum to produce 2-(azepan-1-yl)-1-phenylhexan-1-one hydrochloride (4.8 g, 84%) as a white solid. The compound was confirmed by $^1$H NMR and HPLC.

Example 6: In Vitro Pharmacology

This example tested 1-phenyl-2-(piperidin-1-yl)hexan-1-one (1) and 2-(azepan-1-yl)-1-phenylhexan-1-one (2) in binding, uptake and cellular and nuclear receptor functional assays.

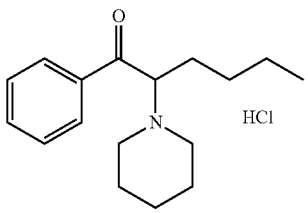

Compound (1)

-continued

Compound (2)

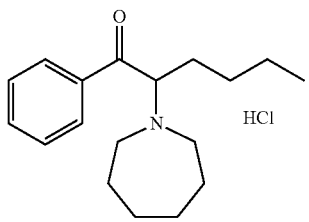

Compounds (1) and (2) were tested at several concentrations for $IC_{50}$ or $EC_{50}$ determination at target receptors. For receptor binding assays, concentrations of ligand that inhibited 50% of radioligand bound ($IC_{50}$) were calculated, and $K_i$ values were determined from $IC_{50}$ values based on the Cheng-Prusoff equation. For receptor function assays, agonist effects were calculated as the concentration of ligand that produced 50% of the maximum agonist control response (e.g., oxotremorine) for each target ($EC_{50}$) and cellular antagonist effects were calculated as the concentration of ligand that produced 50% inhibition of the EC80 agonist control response for each target ($IC_{50}$). For antagonist assays, $K_b$ affinity values were calculated from $IC_{50}$ values using GraphPad Prism 9 (San Diego, Calif. USA).

Initial results showing the pharmacodynamic effects of the test compounds at target receptors are provided in the following tables with detailed pharmacodynamic effects at target MRs shown in figures below.

| Assay | $IC_{50}$ | $K_i$ | $K_b$ | $EC_{50}$ | nH |
|---|---|---|---|---|---|
| Compound (1) | | | | | |
| Dopamine transporter (h) (antagonist radioligand) | 7.2E−08M | 3.8E−08M | | | 1 |
| $M_2$(h) (antagonist effect) | 1.7E−06M | | 1.2E−07M | | |
| Norepinephrine transporter (h) (antagonist radioligand) | 8.7E−06M | 6.5E−06M | | | 1.6 |
| Norephinephrine transporter uptake (h) | 1.3E−06M | | | | |
| Serotonin transporter (antagonist radioligand) | >1.0E−04 | | | | |
| Serotonin transporter uptake | 3.7E−05M | | | | |
| Compound (2) | | | | | |
| Dopamine transporter (h) (antagonist radioligand) | 1.0E−07M | 5.4E−08M | | | 0.9 |
| Dopamine transporter uptake (h) | 7.0E−08M | | | | |
| $M_2$(h) (antagonist effect) | 2.0E−06M | | 1.6E−07M | | |
| Norepinephrine transporter (h) (antagonist radioligand) | 1.3E−05M | 9.8E−06M | | | 0.9 |
| Norephinephrine transporter uptake (h) | 1.1E−06M | | | | |
| Serotonin transporter (antagonist radioligand) | >1.0E−04 | | | | |
| Serotonin transporter uptake | 1.2E−05M | | | | |

The following experimental conditions were used in this example.

| In Vitro Pharmacology: Radioligand Competition Binding Assays | | | | | | | | |
|---|---|---|---|---|---|---|---|---|
| Assay/ Transporters | Source | Ligand | Conc. | $K_d$ | Non-specific | Incubation | Detection Method | Ref. |
| Norepinephrine transporter (h) (antagonist radioligand) | Human recombinant (CHO cells) | [$^3$H]nisoxetine | 1 nM | 2.9 nM | Desipramine (1 μM) | 120 min., 4° C. | Scintillation counting | 1 |
| Dopamine transporter (h) (antagonist radioligand) | Human recombinant (CHO cells) | [$^3$H]BTCP | 4 nM | 4.5 nM | BTCP (10 μM) | 120 min., 4° C. | Scintillation counting | 2 |
| 5-HT transporter (h) (antagonist radioligand) | Human recombinant (CHO cells) | [$^3$H]imipramine | 2 nM | 1.7 nM | Imipramine (10 μM) | 60 min., RT | Scintillation counting | 3 |

1: Pacholczyk, T. et al. Nature (1991) 350, 350-354.

2: Pristupa, Z.B. et al. Mol. Pharmacol. (1994) 45, 125-135.

3: Tatsumi, M. et al. Eur. J. Pharmacol. (1999) 368, 277-283.

| In Vitro Pharmacology: Cellular Receptor Functional Assays | | | | | | |
|---|---|---|---|---|---|---|
| Assay (Receptors) | Source | Stimulus | Incubation | Measured Component | Detection Method | Ref. |
| $M_2$ (h) (agonist effect) | Human recombinant (CHO cells) | None (3 μM acetylcholine for control) | 10 min., 37° C. | cAMP | HTRF | 4 |
| $M_2$ (h) (antagonist effect) | Human recombinant (CHO cells) | Acetylcholine (300 nM) | 10 min., 37° C. | cAMP | HTRF | 4 |

4: Michal, P. et al. Brit. J. Pharmacol. (2001) 132, 1217-1228.

| In Vitro Pharmacology: Monoamine Uptake Assays | | | | | | |
|---|---|---|---|---|---|---|
| Assay (Transporters) | Source | Substrate/ Stimulus Tracer | Incubation | Measured Component | Detection Method | Ref. |
| Norepinephrine transporter uptake (h) | Human recombinant | Norepinephrine hydrochloride-DL-[7-3H(N)] (500 nM) | 120 min. RT | [$^3$H]NE incorporation into cells | Scintillation Counting | 5 |
| Dopamine transporter uptake (h) | Human recombinant | 3H DA (300 nM)/DA (300 nM) | 90 min. RT | [$^3$H]DA incorporation into cells | Scintillation Counting | 6 |
| Serotonin transporter uptake | Rat brain synaptosomes | [$^3$H]5-HT (0.2 μCi/mL) | 15 min. 37° C. | [$^3$H]5-HT incorporation into synaptosomes | Scintillation Counting | 5 |

5: Perovic, S. et al. Arzneim-Forsch. Drug Res. (1995) 45, 1145-1148.
6: Verrico, C. et al. Psychopharmacology (Berl) (2005).

MR Pharmacology

In this example, a novel chemical scaffold for mAChR acting agents is described that permits selectivity for M2Rs versus each of the other four MRs. Based on the α-substituted benzoylethanamine (β-ketoamphetamine) synthetic cathinone backbone, the structures of this example were modified to exhibit mAChR pharmacophore properties with the intention of increasing selective mAChR affinity and decreasing activity of archetypal cathinone targets including the dopamine (DAT), norepinephrine (NET), and serotonin (SERT) transporters.

Figure 1B:
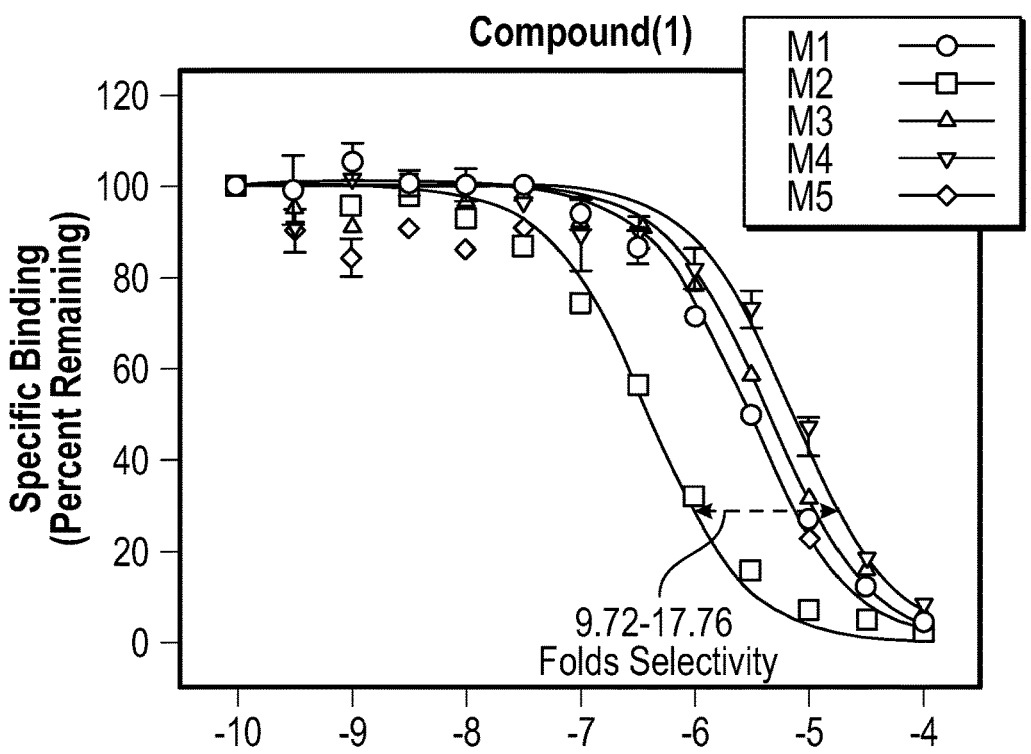
FIG. 1B depicts specific binding data for an embodiment of a compound described herein.
Figure 1C:
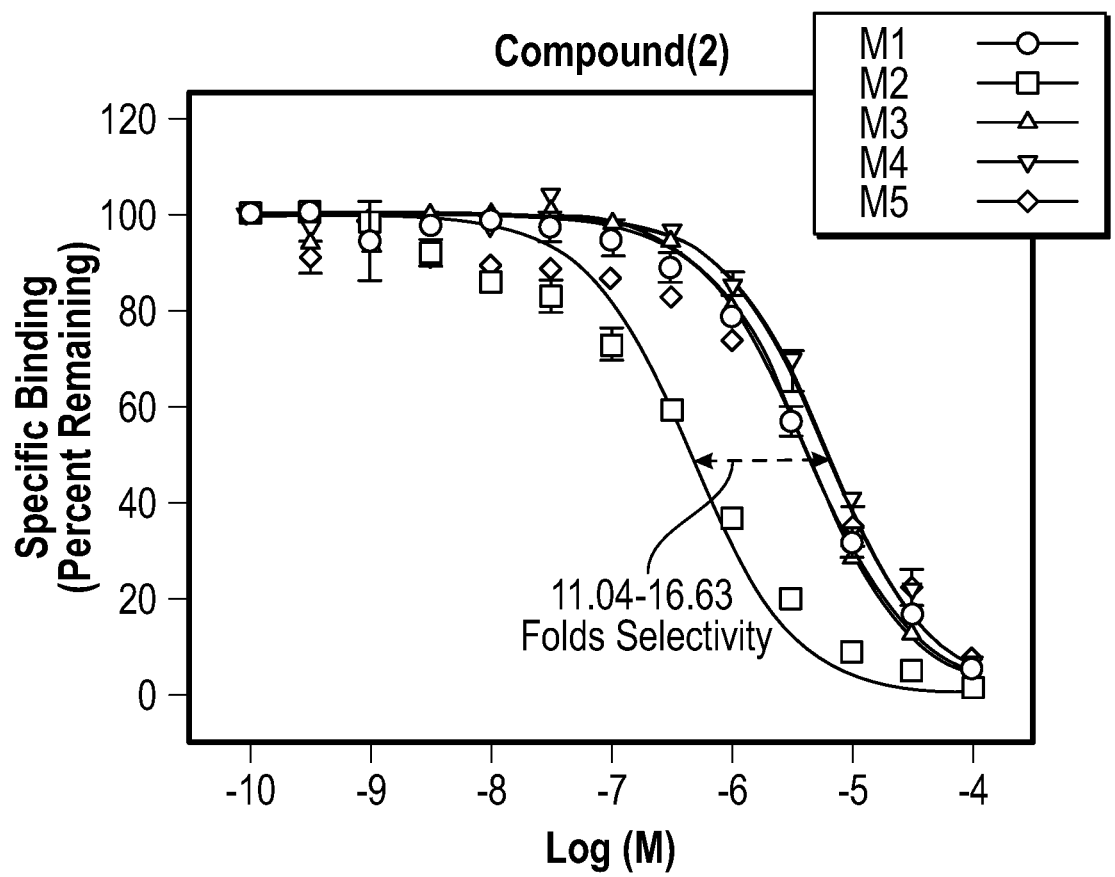
FIG. 1C depicts specific binding data for an embodiment of a compound described herein.

As the following results demonstrate, the initial compounds of this example, termed Compound (1) (1-phenyl-2-(piperidin-1-yl)hexan-1-one) and Compound (2) (2-(azepan-1-yl)-1-phenylhexan-1-one), exhibited nanomolar affinity for the M2R (70 nM and 90 nM, respectively), and had ca. 10-18-fold selectivity for the M2R compared to M1R, M3R, M4R, and M5R (FIG. 1A, FIG. 1B, FIG. 1C; the following table). FIG. 1A, FIG. 1B, and FIG. 1C depict radioligand binding assays of atropine, Compound (1), and Compound (2) binding to human mAChR labeled with [3H]—N-methylscopolamine showed that Compound (1) and Compound (2) were selective ligands at human M2Rs.

TABLE

Affinities of test compounds at human muscarinic M1 (N = 6), M2 (N = 9), M3 (N = 5), M4 (N = 3), M5 (N = 4).

| Affinities, Ki ± SEM, nM | $M_1$ | $M_2$ | $M_3$ | $M_4$ | $M_5$ | $M_2$ Selectivity |
|---|---|---|---|---|---|---|
| Atropine | 1.16 (0.15) | 0.72 (0.09) | 0.63 (0.05) | 0.43 (0.03) | 0.26 (0.04) | 0.36-1.71 |

TABLE-continued

Affinities of test compounds at human muscarinic
M1 (N = 6), M2 (N = 9), M3 (N = 5), M4 (N = 3), M5 (N = 4).

| Affinities, Ki ± SEM, nM | $M_1$ | $M_2$ | $M_3$ | $M_4$ | $M_5$ | $M_2$ Selectivity |
|---|---|---|---|---|---|---|
| Compound 1 | 1005 (286) | 69.86 (13.08) | 993.8 (167.1) | 1241 (401) | 679 (175) | 9.72-17.76 |
| Compound 2 | 1488 (456) | 89.47 (24.26) | 988 (124) | 997 (167) | 1035 (251) | 11.04-16.63 |

Comparatively, the prototypical mAChR antagonist medication, atroprine, has no appreciable selectivity for any of the mAChR subtypes (FIG. 1A, FIG. 1B, FIG. 1C).

Figure 2A:
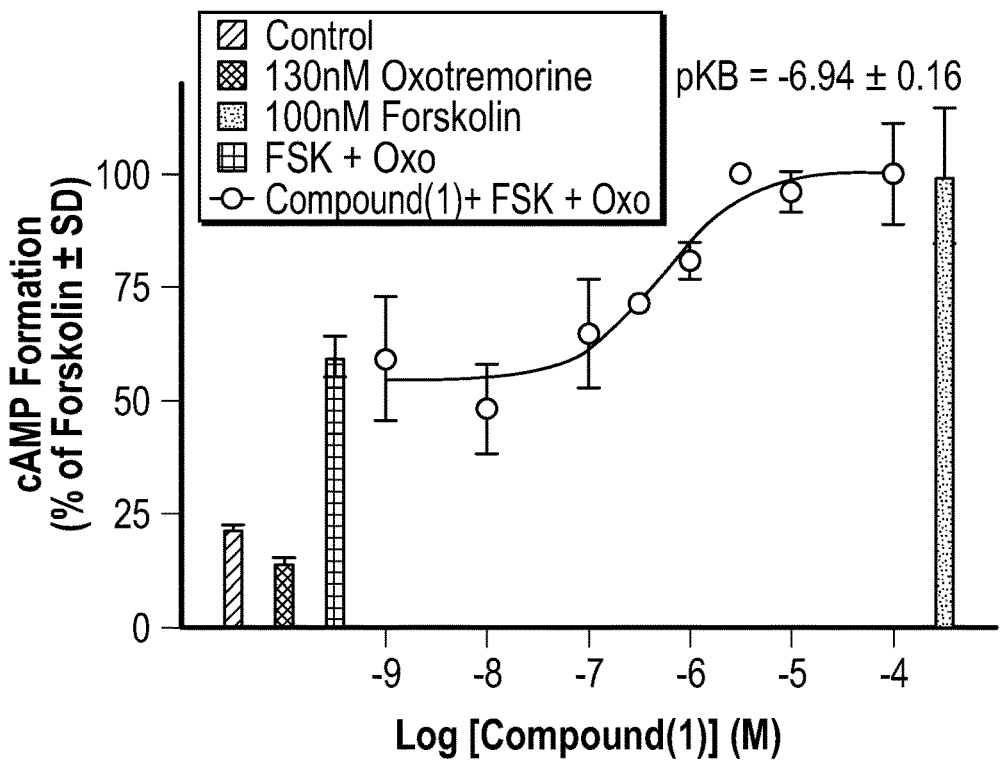
FIG. 2A depicts a plot of antagonism of M2 receptor-mediated cAMP inhibition for an embodiment of a compound described herein.
Figure 2B:
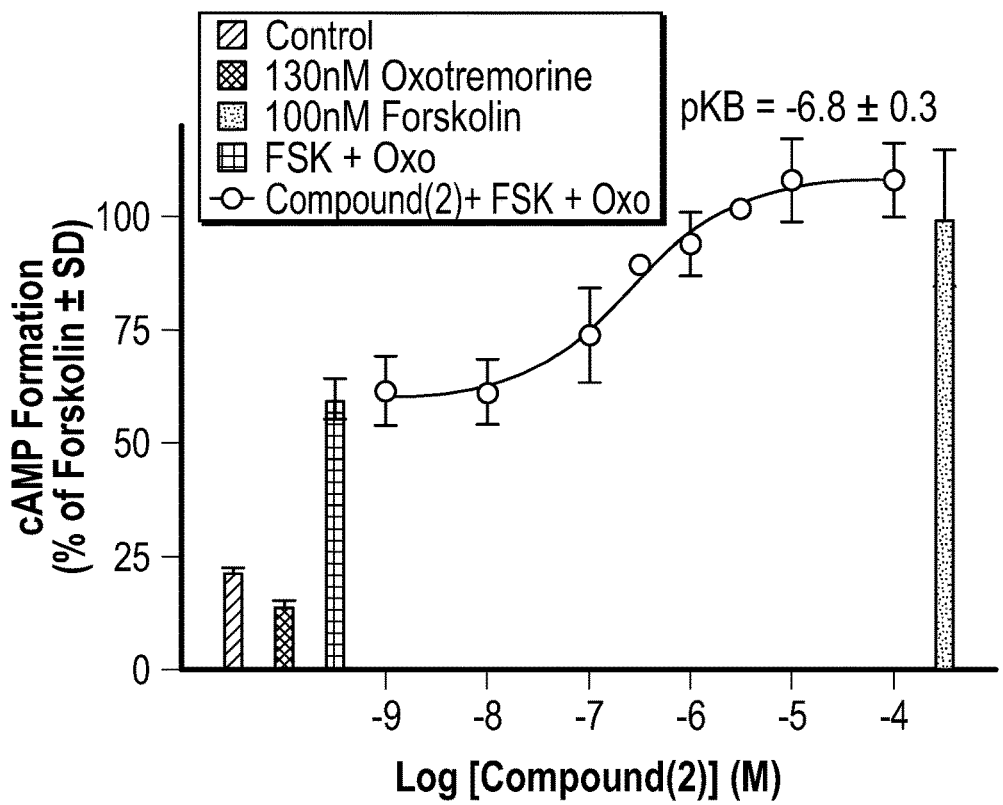
FIG. 2B depicts a plot of antagonism of M2 receptor-mediated cAMP inhibition for an embodiment of a compound described herein.

The M2R coupled to Gαi/o proteins, and its agonism functioned to decrease formation of the intracellular second messenger cyclic-adenosine-monophosphate (cAMP). Using a cellular model of forskolin-induced cAMP formation in clonal cell lines expressing the M2R, it was showed that the mAChR agonist oxotremorine elicited this inhibition of cAMP formation with an EC80 of 130 nM (Chen, Y., and Canal, C. E. (2020) Structure-Activity Relationship Study of Psychostimulant Synthetic Cathinones Reveals Nanomolar Antagonist Potency of alpha-Pyrrolidinohexiophenone at Human Muscarinic M2 Receptors, ACS Chem Neurosci 11, 960-968). In the presence of oxotremorine, an antagonist of the M2R would be expected to reverse the effects of the agonist, thereby increasing cAMP formation. Indeed, the results demonstrated that Compounds (1) and (2) inhibited the effects of EC80 oxotremorine, displaying M2R antagonist activity (FIG. 1B and FIG. 1C) with pKB values of −6.9±0.16 and −6.8±0.29, in line with the nanomolar binding affinity of the agents (FIG. 2A, FIG. 2B; the foregoing table). These pharmacological discoveries were non-obvious, as the current understanding is that synthetic cathinones are agents that solely act at the monoamine transporters (Baumann, M., et al. (2018). Neuropharmacology of Synthetic Cathinones. Handbook of Experimental Pharmacology, 252, 113-142).

Regarding FIG. 2A and FIG. 2B, Compounds (1) and (2) were human M2R antagonists. Compounds (1) and (2) inhibited decreases in cAMP formation induced by stimulation of human M2Rs by oxotremorine (130 nM) in the presence of the adenylyl cyclase activator forskolin (FSK; 100 nM). pKB values (±SD) for each were calculated from three to four independent experiments, with representative figures shown.

Given that these agents are based on the cathinone backbone and that cathinones are known to have high affinity and functional effects at DAT, NET, and SERT neurotransmitter transporters (Baumann, M., et al. (2018). Neuropharmacology of Synthetic Cathinones. Handbook of Experimental Pharmacology, 252, 113-142), which produce psychoactive effects, the affinity and functional effects of Compounds (1) and (2) was assessed at all three transporters. The affinity the α-substituted pyrrolidine-containing-cathinones α-PPP, α-PBP, α-PVP and α-PHP (1-phenyl-2-(pyrrolidin-1-yl) hexan-1-one) (following table) had strong affinity for DAT, NET and SERT with functional antagonist IC50 values ranging from 0.014-0.54 μM for DAT, 0.036-0.14 μM for NET, and 40-188 μM for SERT (Eshleman, A. J., Wolfrum, K. M., Reed, J. F., Kim, S. O., Swanson, T., Johnson, R. A., & Janowsky, A. (2017). Structure-Activity Relationships of Substituted Cathinones, with Transporter Binding, Uptake, and Release. *The Journal of Pharmacology and Experimental Therapeutics*, 360(1), 33. https://doi.org/10.1124/JPET.116.236349).

TABLE

Affinities (Ki) and functional activity (IC50) of test compounds, reference compounds, and α-PHP at human DAT, NET, and SERT. N.B. denotes no binding at 100 μM. N.D. denotes that the value was not determined. Results were obtained by contract with Eurofins/Cerep * Eshleman, A. J., Wolfrum, K. M., Reed, J. F., Kim, S. O., Swanson, T., Johnson, R. A., & Janowsky, A. (2017). Structure-Activity Relationships of Substituted Cathinones, with Transporter Binding, Uptake, and Release. *The Journal of Pharmacology and Experimental Therapeutics*, 360(1), 33.

| | Affinity (Ki) (μM) | | | Uptake Inhibition (IC50) (μM) | | |
|---|---|---|---|---|---|---|
| | DAT | NET | SERT | DAT | NET | SERT |
| Compound 1 | 0.038 | 6.5 | N.B. | 0.047 | 1.3 | 37 |
| Compound 2 | 0.054 | 9.8 | N.B. | 0.070 | 1.1 | 12 |
| α-PHP* | 0.016 | 0.3 | 33 | 0.022 | 0.03 | 40 |
| Reference compounds | | | | | | |
| Protriptyline | N.D. | 0.0026 | N.D. | N.D. | 0.0014 | N.D. |
| BTCP | 0.0066 | N.D. | N.D. | N.D. | N.D. | N.D. |
| Imipramine | N.D. | N.D. | 0.00096 | N.D. | N.D. | 0.04 |
| GBR12909 | N.D. | N.D. | N.D. | 0.004 | N.D. | N.D. |

The results of this example for Compounds (1) and (2) demonstrated, relative to the psychostimulant synthetic cathinone, α-PHP, significantly reduced NET and SERT binding affinity and functional antagonism with affinities of 6.5 µM and 9.8 µM, respectively at NET, with neither compound exhibiting demonstrable binding at SERT. The DAT affinity and functional activity of Compounds (1) and (2) was similar to α-PHP and related analogs (Baumann, M., et al. (2018). Neuropharmacology of Synthetic Cathinones. Handbook of Experimental Pharmacology, 252, 113-142).

In Vivo Activity of Compound (1)

Figure 3:
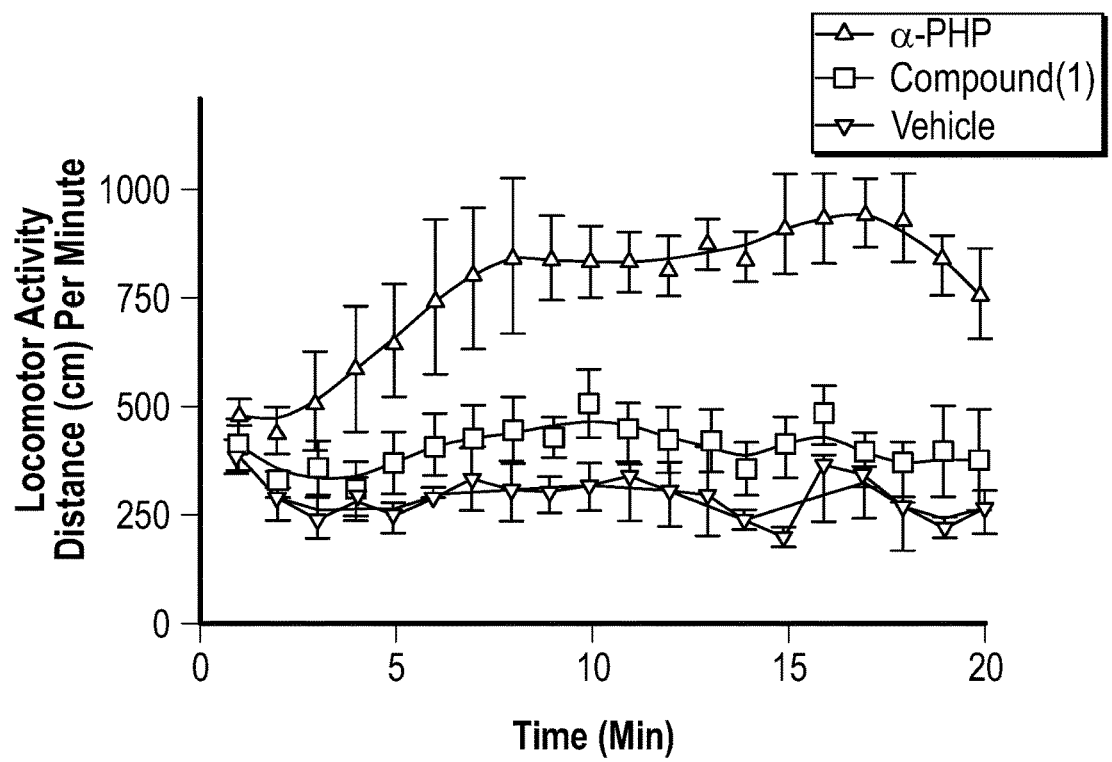
FIG. 3 depicts a plot of locomotor activity for an embodiment of a compound described herein.

Since functional inhibition of neurotransmitter transporters, particularly DAT, is classically known to cause psychomotor stimulation, the ability of Compound (1) to induce this effect in mice was assessed, directly comparing results to α-PHP, a pyrrolidine-substituted analog of Compound (1). Adult male and female mice on the FVB background were injected subcutaneously and then immediately placed inside of an open field chamber, where their activity was recorded automatically for 20-min by an overhead camera connected to a PC running EthoVision XT software. These in vivo locomotor results demonstrated that, as previously reported in the literature, α-PHP (2.8 mg/kg, s.c.) robustly increased locomotor activity compared to vehicle (P<0.0001, FIG. 3). Meanwhile, at the same dose and route of administration, locomotor-stimulating effects of Compound (1) were much lower than α-PHP, with results being highly significant (P<0.0001, FIG. 3), and with Compound (1) eliciting effects that were nearly indistinguishable from vehicle-treated mice (FIG. 3). FIG. 3 depicts in vivo effects of vehicle, α-PHP (2.8 mg/kg, s.c.), and Compound (1) (2.8 mg/kg, s.c.) on locomotor behavior in mice (Ns=6, three male and three female, adult mice per group). α-PHP significantly increased locomotor activity relative to vehicle-treated mice (P<0.0001). The effects of Compound (1) were significantly lower than α-PHP (P<0.0001). Data are means (±SEM).

These in vivo results were non-obvious, as the current understanding is that compounds that inhibit DAT strongly stimulate locomotor activity in mice (Baumann, M., et al. (2018). Neuropharmacology of Synthetic Cathinones. Handbook of Experimental Pharmacology, 252, 113-142). In addition, there is widespread agreement that drugs of abuse stimulate locomotor activity in mice (Roberts, A. J., Casal, L., Huitron-Resendiz, S., Thompson, T., & Tarantino, L. M. (2018). Intravenous cocaine self-administration in a panel of inbred mouse strains differing in acute locomotor sensitivity to cocaine. *Psychopharmacology* 2018235:4, 235(4), 1179-1189. https://doi.org/10.1007/S00213-018-4834-7), the results from Compound (1) provided compelling early evidence that it may have low abuse potential. The M2R antagonism inherent in Compound (1) may counteract the locomotor stimulating effects of DAT inhibition, as stimulation of ACh release via presynaptic blockade of M2R, is known to modulate dopamine levels, that are increased by DAT inhibition. Acetylcholine and dopamine interact closely in the striatum, where dopaminergic neurons express MRs and cholinergic neurons express dopamine receptors (Myslivecek, J. (2021). Two Players in the Field: Hierarchical Model of Interaction between the Dopamine and Acetylcholine Signaling Systems in the Striatum. *Biomedicines* 2021, Vol. 9, Page 25, 9(1), 25. https://doi.org/10.3390/BIOMEDICINES9010025).

Figure 4:
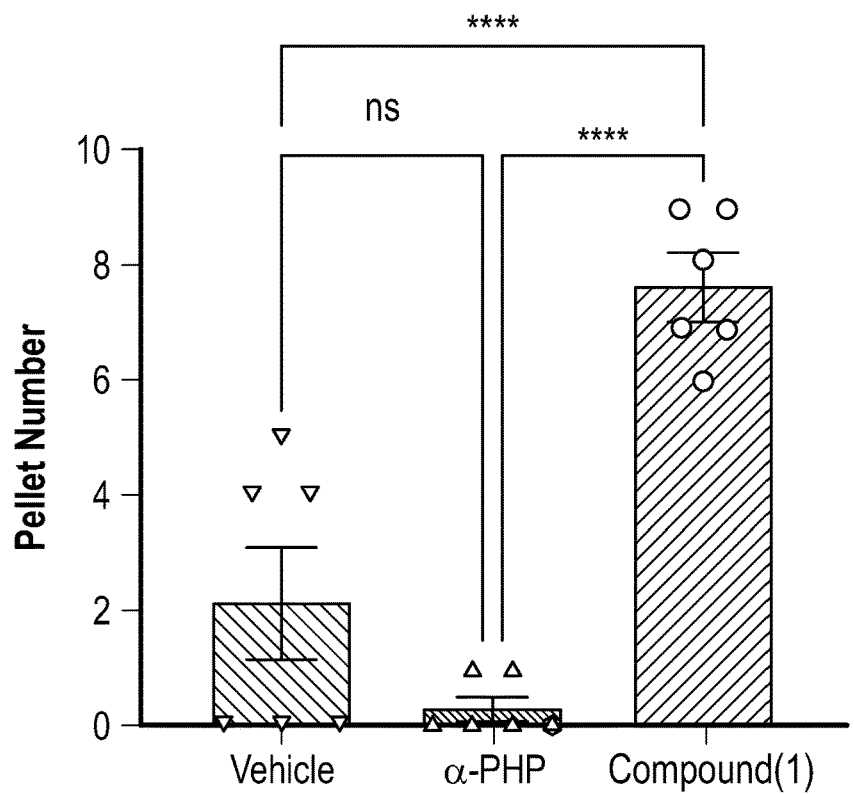
FIG. 4 depicts data demonstrating the increased gastrointestinal mobility caused by an embodiment of a compound described herein.

Consistent with pre-synaptic M2R antagonist activity, also observed was an increase in defecation caused by Compound (1) (FIG. 4). The number of fecal pellets produced by mice that received Compound (1) was significantly higher than both vehicle (p<0.0001) and α-PHP treated mice (p<0.0001), while no significant difference was observed between the vehicle and α-PHP groups. Regarding FIG. 4, Compound (1) (2.8 mg/kg, s.c.) increased gastrointestinal motility compared to vehicle and α-PHP (2.8 mg/kg, s.c.) treated mice. Scatter dot plots with means (±SEMs).

The results of this example demonstrated that Compounds (1) and (2) were selective antagonists of human M2Rs with in vivo activity in mice consistent with an M2R antagonist mechanism. They have decreased binding affinity and functional activity at both NET and SERT, relative to a classic pyrrolidine-containing, psychostimulant, α-PHP. They retained high affinity and functional activity at DAT, but produced significantly less locomotor stimulation than α-PHP. Based on the described role of M2R in cognition, movement (pyramidal and extrapyramidal) learning, memory, cardiac contractility, GIT peristalsis, urinary storage and voiding, as well as airway function, the clinical utilization of these selective M2R antagonists can be used for the listed central and peripheral indications. Compounds (1) and (2) and the other compounds described herein may be used as single pharmacotherapy options to treat various dysfunctions caused, for example, by Parkinson's disease, including motor and non-motor symptoms, such as constipation and cognitive dysfunction (Bloem, B. R., Okun, M. S., and Klein, C. (2021) Parkinson's disease, Lancet 397, 2284-2303; de la Cruz, J., and Canal, C. (2019) Can pimavanserin help patients with Parkinson disease psychosis?, JAAPA 32, 44-45; Metta, V., Leta, V., Mrudula, K. R., Prashanth, L. K., Goyal, V., Borgohain, R., Chung-Faye, G., and Chaudhuri, K. R. (2021) Gastrointestinal dysfunction in Parkinson's disease: molecular pathology and implications of gut microbiome, probiotics, and fecal microbiota transplantation, J Neurol).

Example 7—Nanomolar Antagonist Potency of α-Pyrrolidinohexiophenone (α-PHP) at Human Muscarinic $M_2$ Receptors In this example, the following materials and procedures were used.

α-PPP hydrochloride and MDPPP hydrochloride were synthesized. α-PHP hydrochloride (catalog #9001934), α-PHPP hydrochloride (catalog #14762), 3,4-Methylenedioxy-α-pyrrolidinobutiophenone hydrochloride (MDPBP, catalog #10437), MDPHP (catalog #16361), and 3,4-Methylenedioxy-α-pyrrolidinoheptaphenone hydrochloride (MDPHPP, catalog #16358) analytical standards were purchased from Cayman Chemical (Ann Arbor, Mich., USA). α-PBP hydrochloride (catalog #P-110, 1 mg of free base per mL methanol), α-PVP hydrochloride (catalog #P-090, 1 mg of free base per mL methanol), and MDPV hydrochloride (catalog #M-146, 1 mg of free base per mL methanol) analytical standards were purchased from MilliporeSigma (Darmstadt, Germany). Atropine sulfate monohydrate was purchased from Alfa Aesar (Tewksbury, Mass., USA). Oxotremorine sesquifumarate was purchased from Tocris Bioscience (Minneapolis, Minn., USA). All solid compounds were dissolved in dimethyl sulfoxide to 10 mM concentrations for receptor binding assays, and in Milli-Q® water (MilliporeSigma) to 10 mM concentrations for receptor function assays, prior to diluting in assay buffer. All compounds that were procured as methanol solutions were diluted in assay buffer for receptor binding assays. No drugs procured as methanol solutions were tested in functional assays. [$^3$H]Scopolamine (also known as "[$^3$H]NMS," scopolamine methyl chloride, [$^3$H]—N-Methyl-Scopolamine, N-methyl-[$^3$H]Scopolamine; specific activity 80.1 Ci/mmol) was purchased from Perkin Elmer (Waltham, Mass., USA).

Radioligand Competition Binding: Radioligand competition binding assays were conducted using membranes collected from transiently transfected HEK293 cells (P<20 from a procured stock, CRL-1573, ATCC, Manassas, Va., USA) as previously described (Chen, Y., et al. *Drug Test Anal* 11, 990-998). Briefly, cells ~90% confluent in 10 cm plates were transfected with 5 μg human $M_1R$, $M_2R$, $M_3R$, $M_4R$ or MsR cDNA (cDNA resource center, Bloomsburg, Pa., USA) using a lipid-based method (LipoD293 reagent, SignaGen Laboratories, Rockville, Md., USA). Membranes were collected by centrifugation about 48 hours later and stored at −80° C. until used. For initial affinity estimates, membranes were incubated in 96-well plates with 1 nM [$^3$H]Scopolamine and test compounds in assay buffer at final concentrations of 1 and 10 μM. Atropine (10 μM) was used to define non-specific binding. After a 90-minute incubation at room temperature on a shaker, contents from the plates were rapidly filtered through GF/B fiberglass filter mats, pre-soaked with ice cold 50 mM Tris buffer (pH 7.4), using a Microbeta Filtermat-96 cell harvester (Perkin Elmer, Waltham, Mass., USA). Approximately 200 mL of ice cold, 50 mM Tris buffer was then vacuumed through filter mats to wash away unbound radioligand. Filter mats were dried on a hot plate and soaked in Betaplate (Perkin Elmer, Waltham, Mass., USA) scintillation fluid in plastic bags. Bags were sealed and placed in cassettes. Radioactivity was measured in a Microbeta2 Microplate Counter (Perkin Elmer, Waltham, Mass., USA), and counts per minute corresponding to each well on the plates were recorded. For full dose-response competition binding assays, increasing half-log unit concentrations of five unsubstituted PSCs were tested at $M_2Rs$ and $M_1Rs$, with the same procedures described above.

$M_2R$ cAMP Signaling: cAMP measurements were performed with the cAMP Hunter eXpress® CHRM2 CHO-K1 GPCR assay (Eurofins DiscoveRx, Fremont, Calif., USA) according to the manufacturer's protocol. Briefly, in the provided 96-well tissue culture-treated plate, 100 μL of human $M_2R$ expressing CHO-K1 cells were seeded in cell plating reagent and incubated (37° C., 5% $CO_2$, 95% humidity) overnight. Cell plating reagent was replaced with 30 μL of cell assay buffer the next day. For agonist stimulation, cells were treated with increasing half-log unit concentrations of oxotremorine in the presence of 10 μM forskolin, followed by incubation for 30 minutes. A cAMP antibody, cAMP working detection solution and enzyme acceptor solution were then added according to the protocol, and the final chemiluminescent signals were detected by a Mithras LB 940 microplate reader (Berthold Technologies, Bad Wildbad, Germany). Antagonist tests were run by pretreating cells with increasing half-log unit concentrations of α-PHP, followed by incubation for one hour. Cells were then treated with $EC_{80}$ concentration of oxotremorine (130 nM) and 10 μM forskolin. The same incubation and detection procedure used for agonist assays was used for the remaining steps.

$M_1R$ Phosphoinositide Hydrolysis: The activity of α-PHP at $M_1Rs$ was measured using the IP-One homogeneous time resolved fluorescence (HTRF®) kit (Cisbio, Bedford, Mass., USA). The assay was performed per the manufacturer's protocol with optimization based on published methods (see, e.g., Chen, Y., et al. *Drug Test Anal* 11, 990-998; and Liu, Y. et al. ACS chemical neuroscience 8, 28-39).

Transfection of HEK293 cells with human $M_1Rs$ using LipoD293 reagent was performed as described for radioligand competition binding assays with one exception: The transfection reagent was replaced with normal growth media (Dulbecco's Modified Eagle Medium containing 10% fetal bovine serum) after 8 hours to improve cell viability. Twenty-four hours after transfection, cells were serum starved for 2 hours and plated at 2500 cells per well in 384-well plates. For agonist stimulation, cells were treated with oxotremorine at increasing half-log unit concentrations, and then incubated for 2 hours.

Antagonist tests were run by pretreating cells with increasing half-log unit concentrations of α-PHP and then incubating for 1 hour. Cells were then treated with 500 nM ($EC_{80}$) oxotremorine. The reaction was terminated with lysis buffer containing d2-labeled IP1 and anti-IP1-Cryptate. HTRF resonance energy transfer was measured by a Mithras LB 940 Multimode Microplate Reader (Berthold Technologies, Bad Wildbad, Germany). For all assays, each concentration of oxotremorine was tested in duplicate and α-PHP was tested in triplicate.

Curve Fitting and Statistical Analyses: All data were analyzed by GraphPad 8.3.0 (San Diego, Calif., USA). $K_i$ values were determined from data fit to both one- and two-site models. $K_d$ values of [$^3$H]Scopolamine at each of the MRs (used in the determination of Ki values) were based on, and in nM were: $M_1R$=1.00; $M_2R$=0.34; $M_3R$=0.36; $M_4R$=0.19; $M_5R$=0.45. Since both α-PPP and α-PBP displaced less than 50% of radioligand when tested at the highest concentration (100 μM) in full dose-response competition binding assays, the data were interpolated by adding a 10 mM data point, which was set as non-specific binding. This was also the approach used to determine estimated $K_i$ values for all compounds tested at 1 and 10 μM concentrations only. The reliability of the $K_i$ estimation likely decreased as numbers deviated beyond 10 μM, e.g., for methylenedioxy-containing PSCs at certain MRs (Table 2). $EC_{50}$ and $IC_{50}$ values from functional assays were determined from data fit to the log(agonist) vs. response (three parameters) or log(inhibitor) vs. response (three parameters) model, respectively. $K_b$ values were calculated from $IC_{50}$ values using the Cheng-Prusoff equation with modification (see, e.g., Leff, P., and Dougall, I. G. (1993) *Trends Pharmacol Sci* 14, 110-112):

$$K_b = IC_{50}/((2+([A]/[A_{50}])nH)1/nH-1)$$

where [A] is the $EC_{80}$ concentration of agonist; [$A_{50}$] is the agonist $EC_{50}$; nH is the Hill slope of the agonist, which was constrained to 1.

Abbreviations: α-PPP=α-Pyrrolidinopropiophenone; α-PBP=α-Pyrrolidinobutiophenone; α-PVP=α-Pyrrolidinopentiophenone; α-PHP=α-Pyrrolidinohexiophenone; α-PHPP=α-Pyrrolidinoheptaphenone; MDPPP=3,4-Methylenedioxy-α-pyrrolidinopropiophenone; MDPBP=3,4-Methylenedioxy-α-pyrrolidinobutiophenone; MDPV=3,4-Methylenedioxypyrovalerone; MDPHP=3,4-Methylenedioxy-α-pyrrolidinohexiophenone; MDPHPP=3,4-Methylenedioxy-α-pyrrolidinoheptaphenone; $M_1R$=muscarinic 1 receptor; $M_2R$=muscarinic 2 receptor; $M_3R$=muscarinic 3 receptor; $M_4R$=muscarinic 4 receptor; $M_5R$=muscarinic 5 receptor; MR=muscarinic receptor.

The motivation to evaluate the activity of PSCs at muscarinic receptors emanated from reports that adverse events caused by certain PSCs appear to mimic anticholinergic deliriants. Ten SCs, including five unsubstituted and five methylenedioxy-containing PSCs (Tables 1 and 2, respectively) were initially screened at 1 and 10 μM concentrations in [3H]Scopolamine radioligand competition binding assays to obtain estimated affinities at each of the five MRs subtypes.

TABLE 1

| R | Name | $M_1R$ | $M_2R$ | $M_3R^*$ | $M_4R^*$ | $M_5R^*$ |
|---|---|---|---|---|---|---|
| —$CH_3$ | α-PPP | 3.71 (0.05) | 4.12 (0.05) | N.C. | N.C. | N.C. |
| —$CH_2CH_3$ | α-PBP | 4.12 (0.17) | 4.40 (0.06) | N.C. | N.C. | N.C. |
| —$CH_2CH_2CH_3$ | α-PVP | 5.29 (0.04) | 6.08 (0.10) | 5.22 | 5.09 | 5.38 |
| —$CH_2(CH_2)_2CH_3$ | α-PHP | 5.80 (0.03) | 6.60 (0.04) | 5.78 | 5.71 | 5.82 |
| —$CH_2(CH_2)_3CH_3$ | α-PHPP | 5.71 (0.06) | 6.18 (0.01) | 5.95 | 5.86 | 5.94 |

Structures, abbreviated names and affinities (pK$_i$s (± SEM)) of unsubstituted PSCs at MRs determined from [³H]Scopolamine competition binding (N = 3). Notice that affinities of PSCs at M$_1$Rs and M$_2$Rs improve with increasing α-carbon side chain length up to α-PHP (emboldened). Affinities of α-PPP and α-PBP at M$_1$Rs and M$_2$Rs had to be interpolated (see Methods), as neither drug completely displaced [³H]Scopolamine at 100 µM (see Figure 1).
*Indicates that M$_3$R, M$_4$R, and M$_5$R affinities are estimated pK$_i$s derived from results of [³H]Scopolamine competition binding assays using 1 and 10 µM concentrations of PSCs (N = 2);

TABLE 1-continued

| R | Name | $M_1R$ | $M_2R$ | $M_3R^*$ | $M_4R^*$ | $M_5R^*$ |
|---|---|---|---|---|---|---|

N.C., not calculated; these drugs displaced <5% of radioligand at 10 µM. Estimated M$_1$R and M$_2$R affinities from the 1 and 10 µM spot tests reasonably matched the obtained values from the full dose-response studies (M$_1$Rs and M$_2$Rs). For example, the estimated pK$_i$ values of α-PHP at M$_1$Rs and M$_2$Rs were 5.59 and 6.33, respectively, i.e. less than 2-fold different than values obtained from full- dose response studies. It is therefore believed that affinity values we report at M$_3$Rs, M$_4$Rs, and M$_5$Rs are fair estimates.

Figure 10:
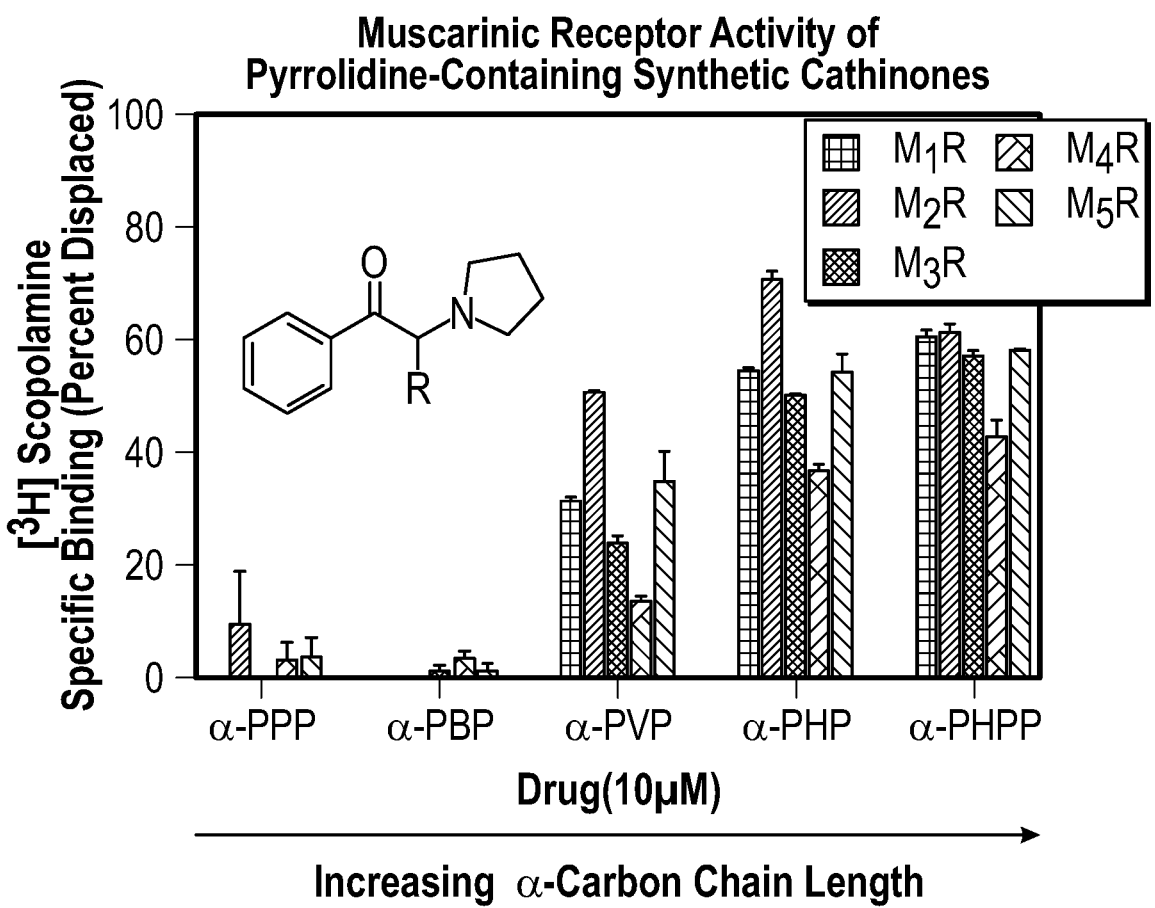
FIG. 10 depicts muscarinic receptor activity of embodiments of compounds described herein.

Additional data are provided at FIG. 10.

In these experiments, the unsubstituted PSCs α-PPP and α-PBP displaced <5% of 1 nM [3H]Scopolamine from each of the MR subtypes at 10 µM, however, increasing the lipophilic, α-carbon side chain length to butyl, α-PHP, caused a precipitous increase in MR binding, providing the initial observations of a SAR for unsubstituted PSCs, which were explored and discuss in detail in the following paragraphs. That the butyl-group on the alpha carbon was ideal, relative to other carbon chains, for binding and selectivity at M2Rs was a non-obvious finding, as it is generally understood that alpha carbon chain lengths beyond propyl-decrease activity at targets. (Krimmer, S. G., Betz, M., Heine, A., and Klebe, G. (2014) Methyl, Ethyl, Propyl, Butyl: Futile But Not for Water, as the Correlation of Structure and Thermodynamic Signature Shows in a Congeneric Series of Thermolysin Inhibitors, Chemmedchem 9, 833-846).

Affinity screens at 1 and 10 µM concentrations showed no consistent SAR for the methylenedioxy-containing analogs (Table 2), except at M$_1$Rs, where, like the unsubstituted PSCs, increasing the lipophilic side chain to butyl, 3,4-Methylenedioxy-α-pyrrolidinohexiophenone (MDPHP), led to increased affinity. The estimated K$_i$ of MDPHP at M$_1$Rs was 3.63 µM—the highest estimated affinity of all methylenedioxy-containing PSCs at MRs. Thus, the bulky, methylenedioxy moiety hindered interaction with MRs.

TABLE 2

| R | Name | $M_1R^*$ | $M_2R^*$ | $M_3R^*$ | $M_4R^*$ | $M_5R^*$ |
|---|---|---|---|---|---|---|
| —$CH_3$ | MDPPP | N.C. | N.C. | N.C. | N.C. | N.C. |
| —$CH_2CH_3$ | MDPBP | N.C. | 4.90 | 4.84 | 4.99 | 4.74 |
| —$CH_2CH_2CH_3$ | MDPV | 5.06 | 4.86 | 4.15 | 5.05 | 5.20 |
| —$CH_2(CH_2)_2CH_3$ | MDPHP | 5.44 | 5.30 | 4.59 | 4.89 | 5.10 |
| —$CH_2(CH_2)_3CH_3$ | MDPHPP | 5.22 | 4.92 | 4.44 | 4.48 | 5.25 |

Structures, abbreviated names and estimated affinities (pK$_i$s) of methylenedioxy-containing PSCs at MRs.
*Note that all MR affinities are estimates derived from results of [³H]Scopolamine competition binding assays using 1 and 10 µM concentrations of PSCs (N = 2);
N.C., not calculated, is defined here as minimal (<5%) to no displacement of radioligand at 10 µM.

Figure 5:
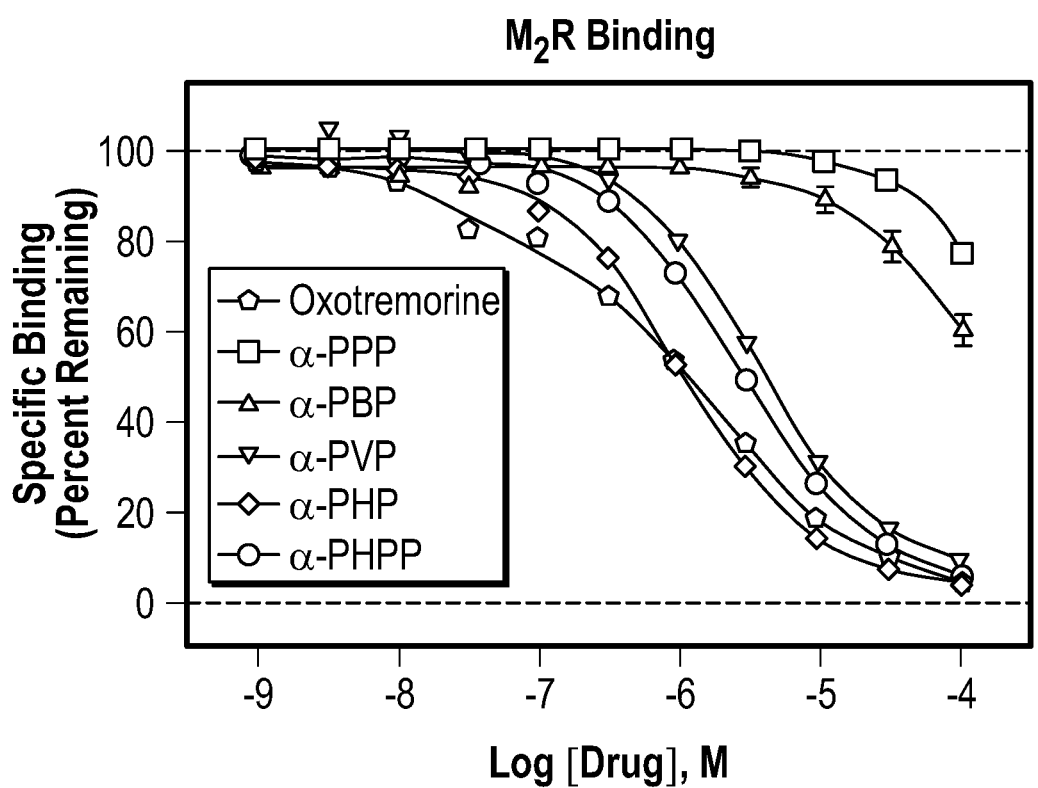
FIG. 5 depicts binding data for embodiments of compounds described herein.

M$_2$Rs are the highest expressed MR in the heart and urinary bladder, and M$_1$Rs are the highest expressed MR in the brain (see, e.g., Lebois, E. P. et al. (2018) Neuropharmacology 136, 362-373; and Frazier, E. P., et al. (2008) Naunyn Schmiedebergs Arch. Pharmacol. 377, 449-462), organs impacted by PSCs, such as α-PHP. Thus, attention was focused on the activity of unsubstituted PSCs at M$_2$Rs and M$_1$Rs. Full dose-response [³H]Scopolamine competition binding experiments were performed with the five unsubstituted PSCs at M$_2$Rs and M$_1$Rs; the MR agonist, oxotremorine, and the MR antagonist, atropine, were included as controls. FIG. 5 shows competition binding curves at M$_2$Rs for the unsubstituted PSCs and oxotremorine. As shown in Table 1 (and confirming initial estimates), the affinity of unsubstituted PSCs at $M_2Rs$ and $M_1Rs$ increased stepwise with increasing side chain length up to butyl, α-PHP.

Data of FIG. 5 are expressed as normalized means (±SEM) of three, independent determinations, with drugs tested at each concentration in triplicate, except for oxotremorine, which was tested in duplicate. Curves for PSCs were best fit with a one-site model, whereas the oxotremorine curve best fit to a two-site model, suggestive of oxotremorine's agonist activity, recognizing agonist high and low affinity $M_2R$ conformations. Note that α-PHP exhibited the highest $M_2R$ activity of all PSCs tested.

There was, first, a drastic leap in affinity from α-PPP to α-PVP. For example, the affinities ($K_i$ values) of α-PPP and α-PBP at $M_2Rs$ were 73 μM and 40 μM, respectively, whereas the $K_i$ of α-PVP at $M_2Rs$ was 824 nM—an 89-fold and 49-fold increase in affinity compared to α-PPP and α-PBP, respectively. The $K_i$ of α-PHP at $M_2Rs$ was 251 nM—a striking 302-fold increase in $M_2R$ affinity compared to α-PPP. At $M_1Rs$, from α-PPP to α-PHP, there was a similarly striking 121-fold increase in affinity. With an additional carbon, α-Pyrrolidinoheptaphenone (α-PHPP), there was a modest decrease in affinity at $M_2Rs$ and $M_1Rs$. α-PVP, α-PHP, and α-PHPP exhibited modestly higher affinity for $M_2Rs$ compared to $M_1Rs$, and like $M_2Rs$, α-PHP possessed highest $M_1R$ affinity relative to all other unsubstituted PSCs. Considering estimated affinities at $M_3Rs$, $M_4Rs$, and $M_5Rs$, all unsubstituted PSCs had lowest affinity at $M_4Rs$. Based on these results, it was concluded that a butyl side chain on unsubstituted PSCs is optimal for binding $M_2Rs$ and $M_1Rs$.

The massive impact of the α-carbon chain length of unsubstituted PSCs on $M_2R$ and $M_1R$ potency indicated it was a critical determinant for interaction with MRs. Moreover, the impact was remarkably greater than what has been reported for binding of unsubstituted PSCs at DAT and NET—the primary targets of PSCs; the affinity of α-PHP at DAT and NET was 81-fold and 6-fold higher than α-PPP, respectively (Eshleman, A. J. et al. (2017) J Pharmacol. Exp. Ther. 360, 33-47). Unsubstituted PSCs with extended alkyl chains were significantly more cytotoxic than methylenedioxy-substituted PSCs, including the extremely potent DAT inhibitor, MDPV (Wojcieszak, J. et al. (2016) Neurotox. Res. 30, 239-250 ("Wojcieszak et al."). For example, Wojcieszak et al. reported that α-Pyrrolidinooctanophenone (α-PV9), containing six carbons in the alkyl chain, potently decreased mitochondrial activity, and severely damaged cellular membranes; this effect was not observed with MDPV. Furthermore, according to Wojcieszak et al., these toxic effects were not observed with cathinones that do not possess the 1-pyrrolidinyl ring, e.g., methcathinone. Thus, three features of SCs appear to impart greater toxicity while concomitantly rendering muscarinic receptor activity: 1) the presence of the 1-pyrrolidinyl ring; 2) alkyl chains extending to at least propyl; 3) the absence of a methylenedioxy moiety. Abuse of MDPV can be associated with numerous side-effects and has been associated with several mortalities; therefore it is possible, if not likely, that its extremely high potency at blocking DAT and NET (e.g., its high sympathomimetic activity) could be a contributing factor, or that other off-targets apart from MRs, contribute to its clinical toxicity.

Figure 6A:
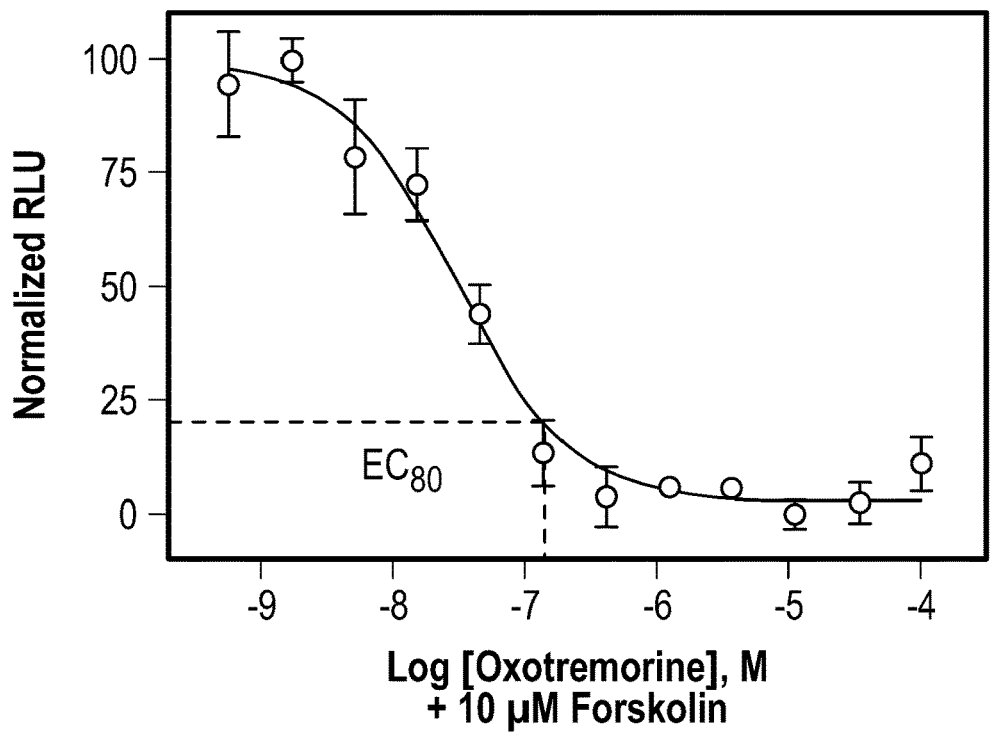
FIG. 6A depicts a plot of $M_2R$-mediated inhibition of forskolin-stimulated cAMP production for a known $M_2R$ agonist.
Figure 6B:
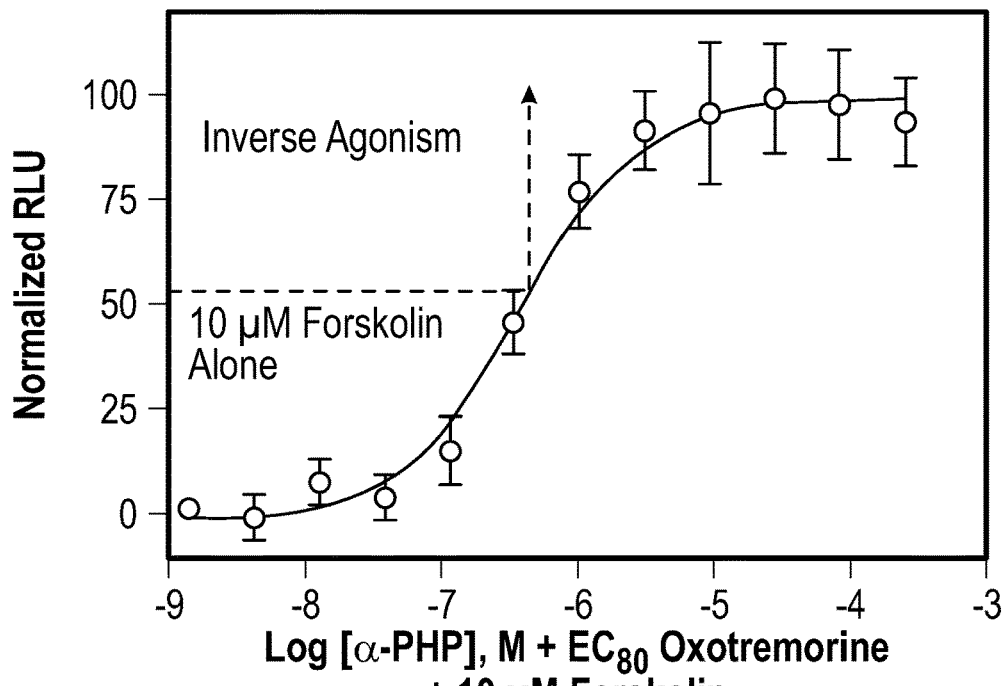
FIG. 6B depicts a plot of $M_2R$-mediated inhibition of the activity of a known $M_2R$ agonist for an embodiment of a compound described herein.

To test whether α-PHP displays antimuscarinic properties, first, its functional capability to interfere with the agonist response of oxotremorine at $M_2Rs$ was assessed. Conducted were cell-based, $M_2R$-cAMP and $M_2R$-arrestin recruitment assays, with $EC_{80}$ concentrations of oxotremorine [80% of the maximum effective concentration—a concentration chosen to maximize signal-to-noise without reducing sensitivity to detect antagonist effects], and a range of concentrations of α-PHP, spanning its affinities obtained from radioligand competition binding experiments. As shown at FIG. 6A and FIG. 6B, the positive control agonist, oxotremorine, decreased forskolin-stimulated cAMP production with an $EC_{50}$ of 29 nM ($pEC_{50}$=7.54±0.12), and an $EC_{80}$ of 130 nM (FIG. 6A); analysis of [$^3$H]Scopolamine $M_2R$ competition binding results showed that oxotremorine data best fit to a two-site model ($R^2$=0.98; F (2, 60)=23.02, P<0.0001, relative to a one-site model; $pK_i$ High=7.92±0.40; $pK_i$ Low=6.15±0.10), consistent with its agonist activity. α-PHP completely inhibited $M_2R$ stimulation by oxotremorine, with a potency, $K_b$, of 120 nM ($pK_b$=6.92±0.03) (FIG. 6B).

Regarding FIG. 6A and FIG. 6B, α-PHP was an antagonist/inverse agonist of M2R-cAMP signaling with nanomolar potency. As depicted at FIG. 6A, Oxotremorine dose-dependently decreased 10 μM forskolin-stimulated cAMP production; data are reported as percentages of the maximal, normalized relative luminescence units (RLU) produced by forskolin alone. As depicted at FIG. 6B, α-PHP blocked effects of oxotremorine (EC80 concentration) at M2Rs, and moreover, increased cAMP levels beyond levels stimulated by forskolin alone, suggesting inverse agonist activity. Data are shown as normalized means (±SEM) from two, independent determinations, with oxotremorine tested at each concentration in duplicate and α-PHP tested at each concentration in quadruplicate.

The maximal effect of α-PHP on cAMP production was above the effect of forskolin alone, which suggested basal (or constitutive) $M_2R$ activity that was blocked by α-PHP. Thus, α-PHP was likely an inverse agonist of the $M_2R$-cAMP signaling pathway. α-PHP exhibited similar pharmacology but had lower potency to block oxotremorine-stimulated β-arrestin recruitment to $M_2Rs$ (FIG. 7A and FIG. 7B).

Figure 7A:
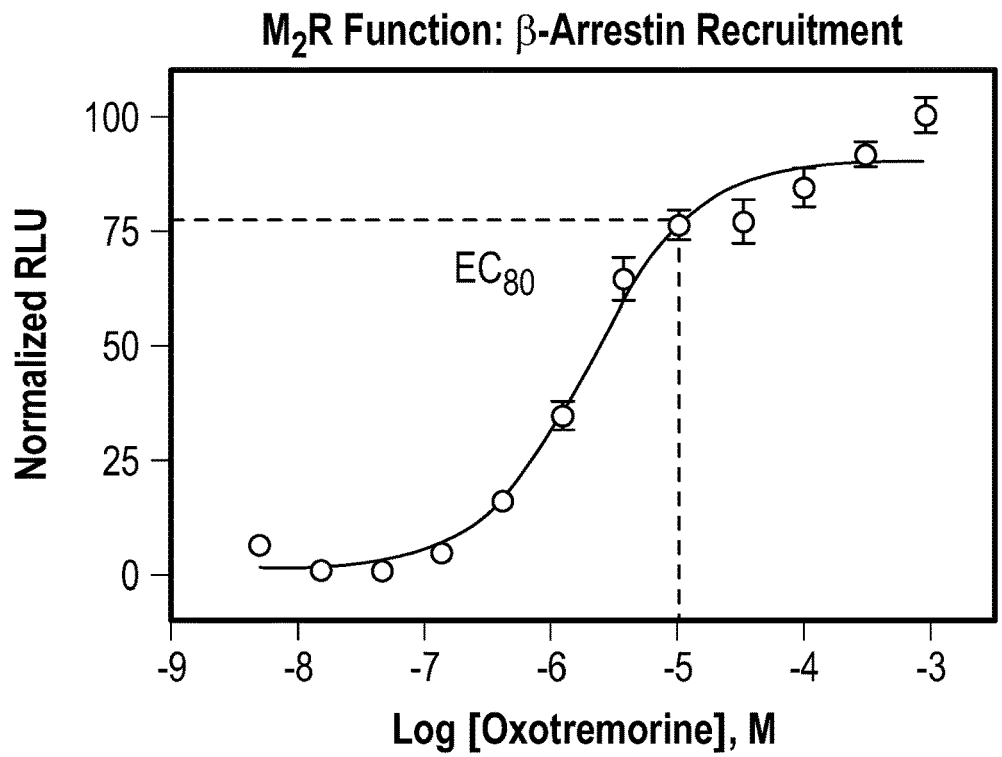
FIG. 7A depicts data related to the $M_2R$ function of a known $M_2R$ agonist compound.
Figure 7B:
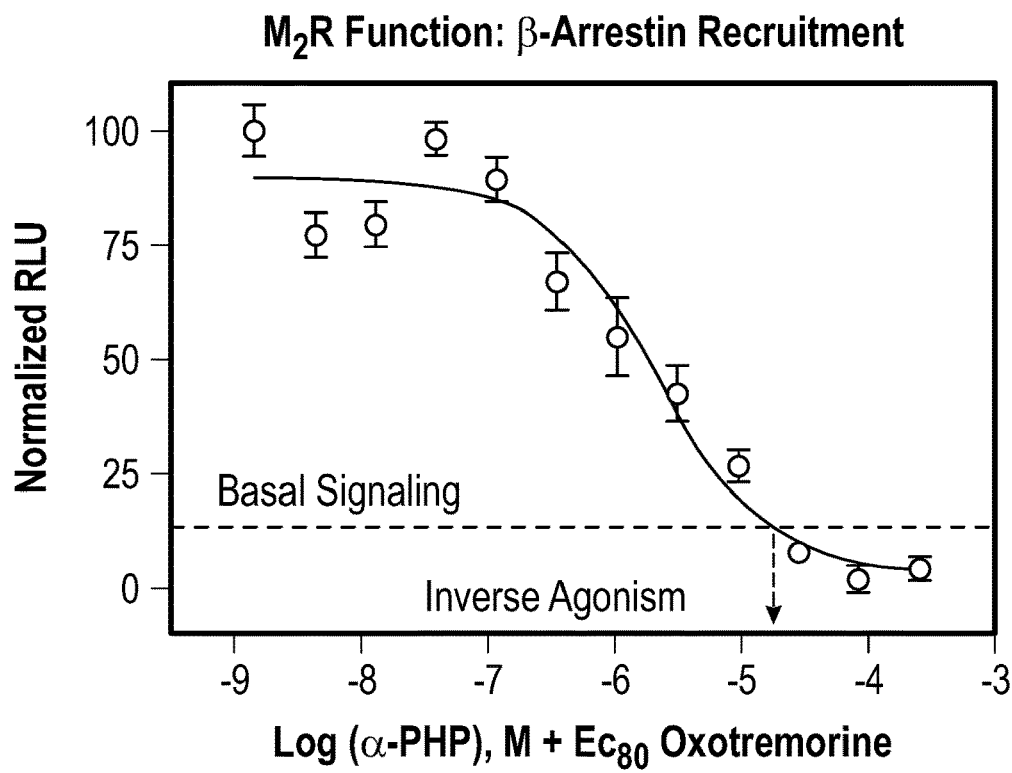
FIG. 7B depicts data related to the $M_2R$ function of an embodiment of a compound described herein.

Regarding FIG. 7A and FIG. 7B, α-PHP was an antagonist/inverse agonist of M2R-β-arrestin recruitment with nanomolar potency. FIG. 6A depicts oxotremorine dose-dependently stimulated β-arrestin recruitment. FIG. 6B depicts α-PHP blocked effects of oxotremorine (EC80 concentration) at M2Rs, and moreover, decreased β-arrestin recruitment below basal* levels, which suggested inverse agonist activity. Data are shown as normalized means (±SEM) of two, independent determinations, with oxotremorine tested at each concentration in duplicate and α-PHP tested in quadruplicate. [*Basal signaling is defined as the normalized RLU emitted by untreated cells.]

Oxotremorine increased β-arrestin recruitment with an $EC_{50}$ of 1.95 μM ($pEC_{50}$ of 5.71±0.11). α-PHP completely inhibited oxotremorine-stimulated β-arrestin recruitment with a $K_b$ of 501 nM ($pK_b$=6.30±0.12), and α-PHP's maximal effect extended below basal signaling, which suggested α-PHP was also an inverse agonist of $M_2R$-β-arrestin recruitment. Also tested was atropine as a control in this assay. Its $K_b$ at $M_2Rs$ was 2.57 nM ($pK_b$=8.59±0.00), and it appeared as a neutral antagonist. The $K_b$ for atropine was consistent with the $K_i$ obtained, 1.26 nM ($pK_i$=8.90±0.07; best fit to a one-site model) from [3H]Scopolamine competition binding (data not shown)—a value close to other observations ($pK_i$=8.91), i.e., as reported on the Psychoactive Drug Screening Program $K_i$ database.

$M_2Rs$ in the heart are essential for controlling chronotropic activity (Gordan, R. et al. World J. Cardiol. 7, 204-214). Parasympathetic, autonomic activation of cardiac $M_2Rs$ lowers heart rate to maintain normal physiological rhythms. Blocking these receptors causes tachycardia. The MR antagonist, atropine, for example, is used in hospitals to treat bradycardia, increasing heart rate, and tachycardia is a well-characterized side effect of atropine used medicinally for other conditions. It was observed that α-PHP acts as a potent antagonist at $M_2R$, which may contribute to the reportedly higher tachycardia associated with α-PHP; according to the World Health Organization's Critical Review Report on α-PHP, tachycardia is an extremely common side effect, and some consumers report that it is stronger than other PSCs; though, one must be mindful of the inherent subjectivity and perhaps inaccuracies associated with self-reports. Cardiovascular events are a primary cause of death associated with PSCs[2]. Owing to its relatively short history as a drug of abuse, the clinical toxicology data on α-PHP are scant relative to other PSCs, like α-PVP, but given the high structural similarity between the two, it is possible, if not likely, that they have similar pharmacological actions at MRs. In one study where α-PVP was analytically confirmed to be the only stimulant responsible for 42 cases of intoxication, 80% of the patients presented with tachycardia (Beck, O. et al. (2016) Clin. Toxicol. 54, 568-575). While this is attributed to sympathomimetic activity, e.g., increased norepinephrine release, the cardiological mechanism of α-PVP could also involve activity at $M_2Rs$; it was found that α-PVP binds $M_2R$ with a $K_i$ of 824 nM, well within the range of postmortem blood concentrations detected in humans, i.e., up to 86 μM. $M_2Rs$ are also the highest expressed MR in the urinary bladder, where they contribute to detrusor smooth muscle contraction, resulting in urination. Side effects of α-PHP include suppression of urinary urgency, which could also be associated with its $M_2R$ antagonist activity. However, it must be acknowledged that pharmacology and gene knockout studies show that $M_3Rs$ are the predominant MR subtype mediating bladder contraction[33,34], and that sympathomimetic actions also can cause urinary retention.

Figure 8:
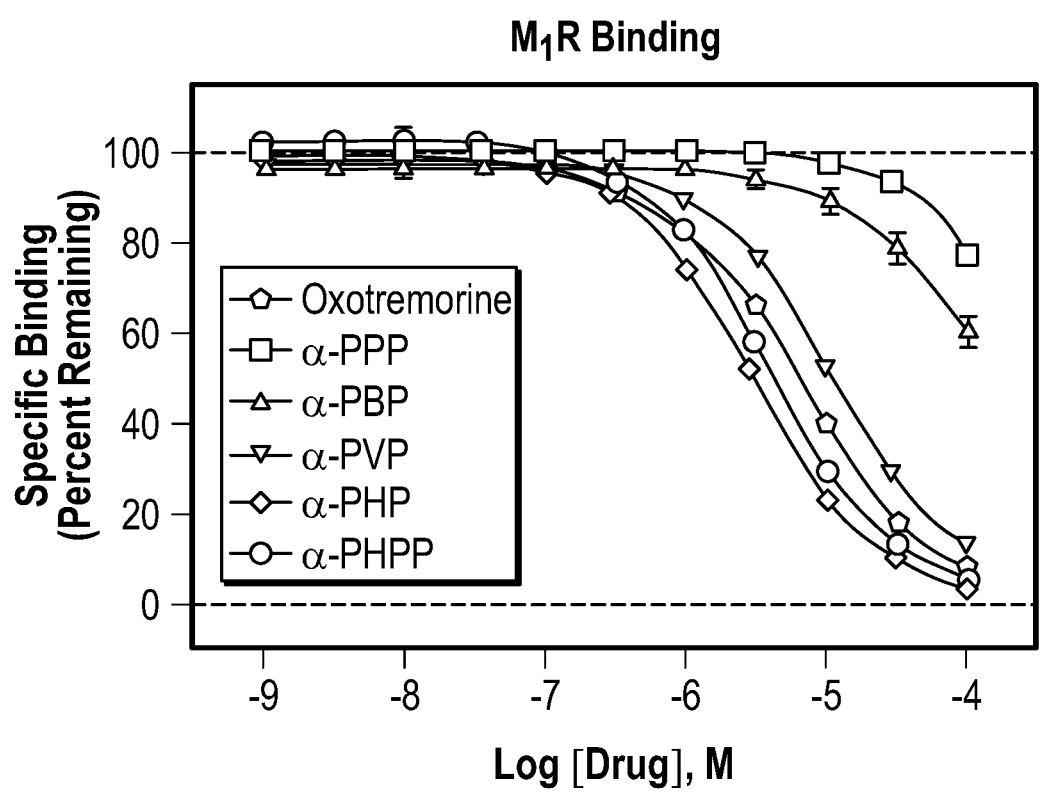
FIG. 8 depicts data related to $M_1R$ binding for embodiments of compounds described herein.
Figure 9A:
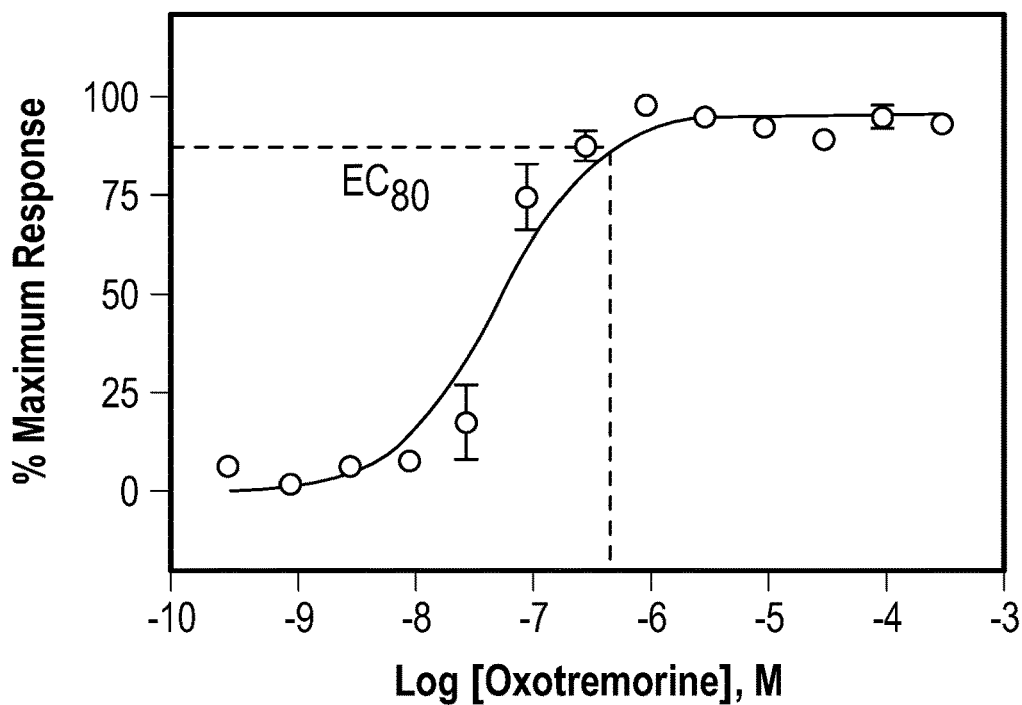
FIG. 9A depicts data related to $M_1R$ function for a known compound.
Figure 9B:
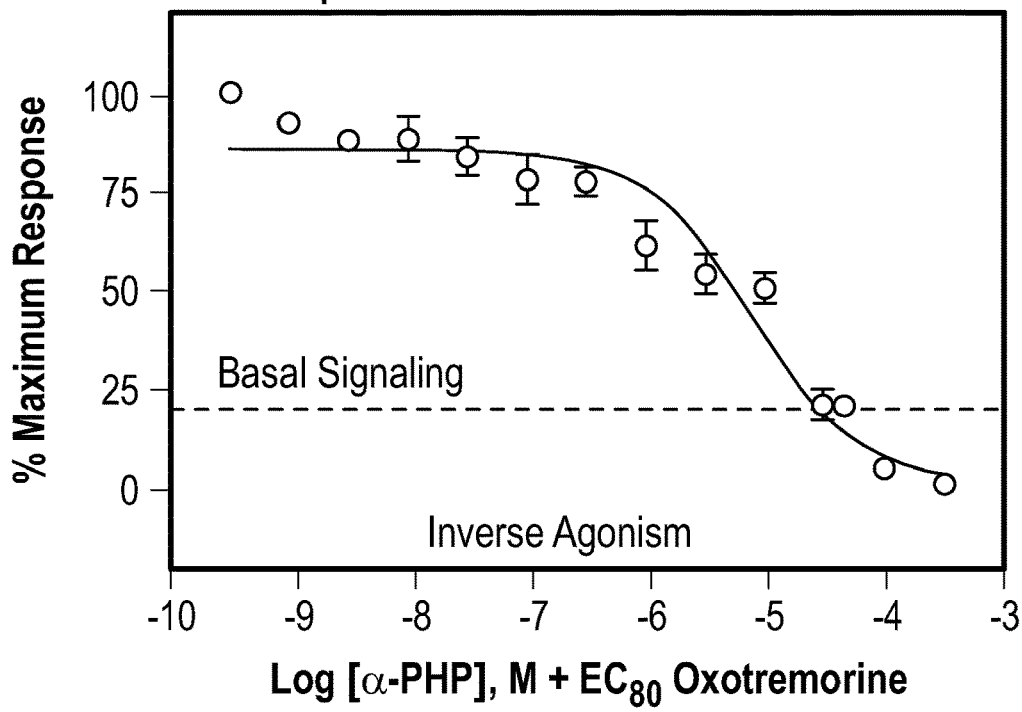
FIG. 9B depicts data related to $M_1R$ function for an embodiment of a compound described herein.

Because PSCs, including α-PHP, can produce cognitive side effects, including symptoms of delirium, such as memory impairment, also determined was the activity of α-PHP at $M_1Rs$ (FIG. 8 and FIG. 9) that are highly expressed in brain regions implicated in symptoms of delirium, including the hippocampus, cortex, and striatum. FIG. 8 depicts results from [$^3$H]Scopolamine $M_1R$ competition binding experiments and illustrates that α-PHP has the highest affinity at $M_1R$ ($K_i$=1.6 μM) relative to the other unsubstituted PSCs. Conducted were cell-based, $M_1R$-phosphoinositide hydrolysis assays, with $EC_{80}$ concentrations of oxotremorine, and a range of concentrations of α-PHP, spanning its affinities obtained from radioligand competition binding experiments. As shown at FIG. 9A and FIG. 9B, the positive control agonist, oxotremorine, increased inositol phosphate 1 (IP1) production with an $EC_{50}$ of 62 nM (pEC=7.21±0.20), and an $EC_{80}$ of 500 nM (FIG. 9A); in $M_1R$ competition binding assays, oxotremorine data best fit to a two-site model ($R^2$=0.98, F (2, 94)=4.01, P=0.0214, relative to a one-site model; $pK_i$ High=7.62±0.36; $pK_i$ Low=5.41±0.04) consistent with its $M_1R$ agonist activity. The affinity of atropine at $M_1Rs$ was 1.55 nM (pKi=8.81±0.05), determined from [$^3$H]Scopolamine competition binding (data not shown; atropine was not evaluated in $M_1R$ functional assays). α-PHP completely inhibited $M_1R$-IP1 production caused by oxotremorine, with a potency, $K_b$, of 1.38 μM ($pK_b$=5.86±0.35) (FIG. 9B). The maximal effect of α-PHP was below basal signaling, which suggested $M_1R$ constitutive activity that was blocked by α-PHP. Thus, like its activity at $M_2Rs$, α-PHP displayed inverse agonist activity at the $M_1R$-inositol phosphate signaling pathway.

It was noted that since α-PHP exhibited inverse agonist activity at $M_2Rs$ and $M_1Rs$ while employing experimental methods to determine functional affinity as described by Kenakin (Kenakin, T. P. (2014) *A pharmacology primer: techniques for more effective and strategic drug discovery*, 4th ed., Academic Press, Amsterdam; Boston), reported α-PHP $K_b$ values may be higher/less potent than actuality. α-PHP's $IC_{50}$ includes concentrations that extend beyond $M_2R$ and $M_1R$ constitutive activity, i.e., beyond complete interference of oxotremorine-elicited (FIG. 8). [$^3$H]Scopolamine competition binding at $M_1Rs$ revealed low micromolar affinity of α-PHP. Data are expressed as normalized means (±SEM) of three, independent determinations, with drugs tested at each concentration in triplicate. Curves for PSCs were best fit with a one-site model, whereas the oxotremorine curve best fit to a two-site model, suggestive of oxotremorine's agonist activity, recognizing agonist high and low affinity $M_1R$ conformations. Note that α-PHP exhibited the highest $M_1R$ activity of all PSCs tested.

Specifically, at FIG. 9, α-PHP is an antagonist/inverse agonist of $M_1R$-inositol phosphate signaling with low micromolar potency. At FIG. 9A, oxotremorine dose-dependently stimulated inositol phosphate 1 (IP1) production. At FIG. 9B, α-PHP blocked effects of oxotremorine ($EC_{80}$ concentration) at $M_1Rs$, and moreover, decreased IP1 production below basal levels, suggesting inverse agonist activity. Data are expressed as normalized means (±SEM) of three, independent determinations, with oxotremorine tested at each concentration in duplicate and α-PHP tested at each concentration in triplicate.

$M_2R$ and $M_1R$ signaling; if one were to determine α-PHP's $IC_{50}$ using concentrations where it fully blocked oxotremorine signaling, but did not reduce basal activity, then its $IC_{50}$ would be shifted to the left; its calculated $K_b$ would then be lower. This may not be an acceptable practice, so conventions were applied in this example.

The invention claimed is:

1. A compound of formula (I), formula (II), or formula (III), or a salt of formula (I), formula (II), or formula (III):

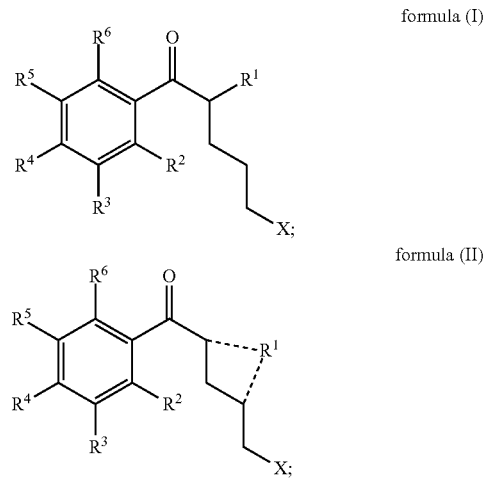

formula (I)

formula (II)

formula (III)

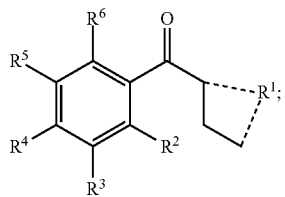

wherein $R^1$ is a $C_1$-$C_{10}$ hydrocarbyl comprising a nitrogen atom;

wherein $R^2$, $R^3$, $R^4$, $R^5$, and $R^6$ are independently selected from the group consisting of hydrogen, methyl, methoxy, hydroxy, a first halogen, and a $C_1$-$C_6$ hydrocarbyl comprising a covalent bond between $R^2$ and $R^3$, $R^3$ and $R^4$, $R^4$ and $R^5$, or $R^5$ and $R^6$; and wherein X is selected from the group consisting of hydrogen, methyl, ethyl, hydroxy, and a second halogen; and wherein (i) $R^1$ is an 8-methyl-8-azabicyclo[3.2.1]octanyl, or (ii) the compound of formula (I), formula (II), or formula (III) is a structure, or a salt thereof, selected from the group consisting of—

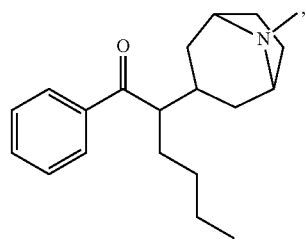

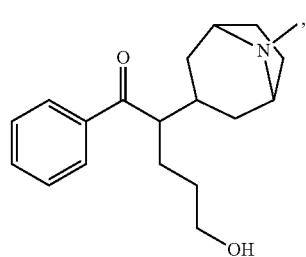

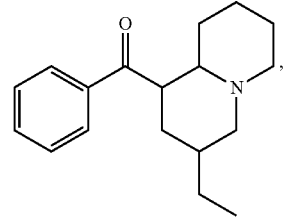

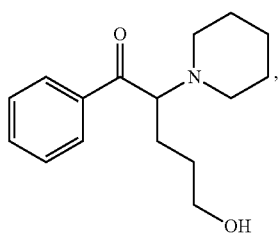

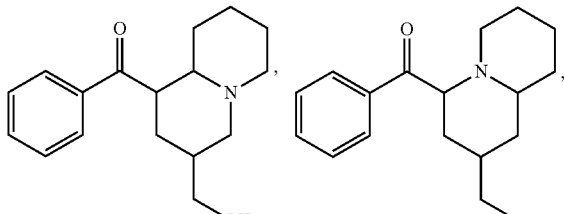

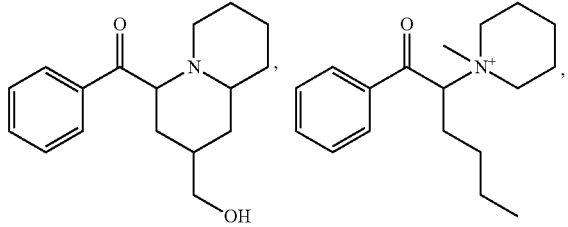

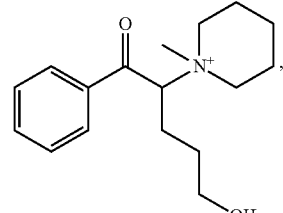

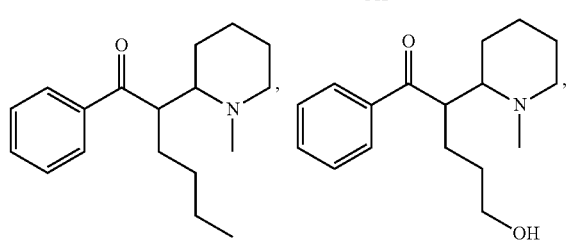

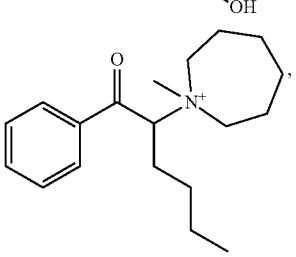

-continued
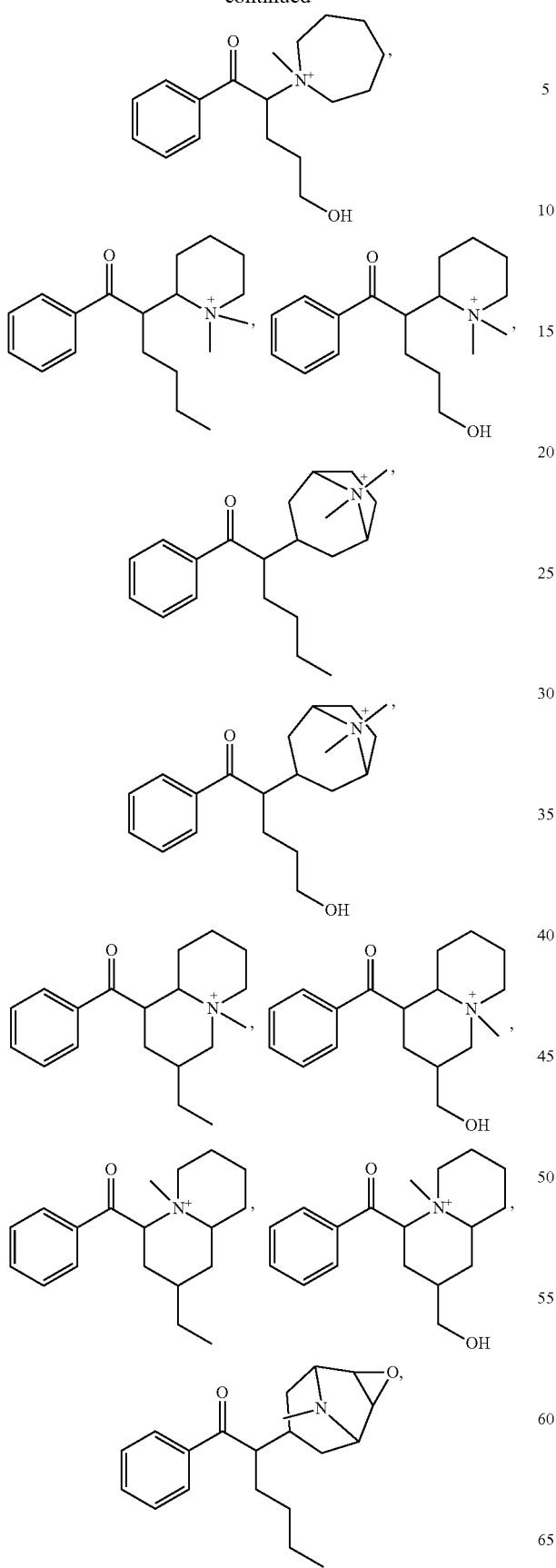
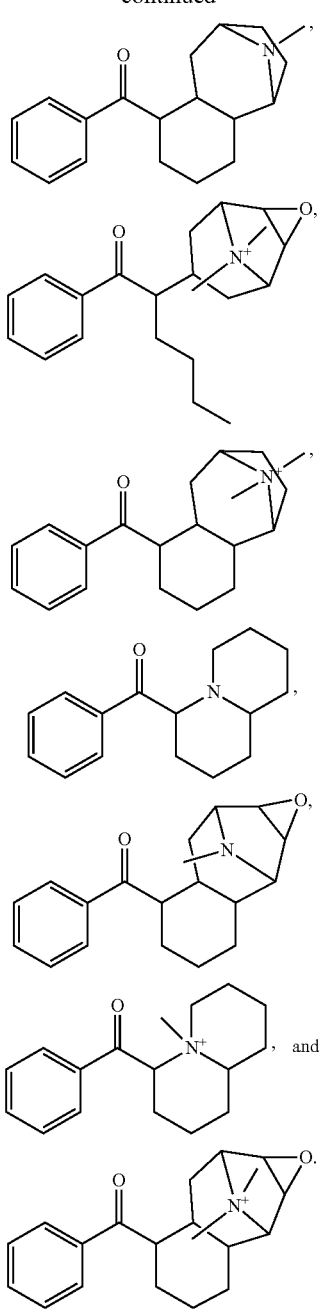
2. The compound of claim 1, wherein the nitrogen atom is a tertiary nitrogen atom.
3. The compound of claim 1, wherein—
(i) $R^1$ is 8-methyl-8-azabicyclo[3.2.1]octan-3-yl,
(ii) $R^2$, $R^3$, $R^4$, $R^5$, and $R^6$ are hydrogen,
(iii) X is methyl, and the compound is 2-(8-methyl-8-azabicyclo[3.2.1]octan-3-yl)-1-phenylhexan-1-one:

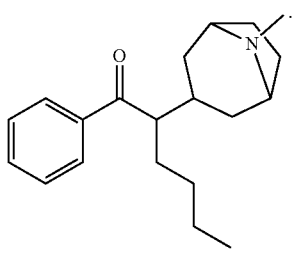 [SMILES: CCCCC(C(=O)c1ccccc1)C1CC2CCC(C1)N2C]

4. The compound of claim 1, wherein $R^1$ is an unsubstituted or substituted piperidinyl.

5. The compound of claim 1, wherein—
 (A)(i) $R^1$ is an unsubstituted piperidin-1-yl,
 (ii) $R^2$, $R^3$, $R^4$, $R^5$, and $R^6$ are hydrogen,
 (iii) X is hydroxy, and the compound is 5-hydroxy-1-phenyl-2-(piperidin-1-yl)pentan-1-one:

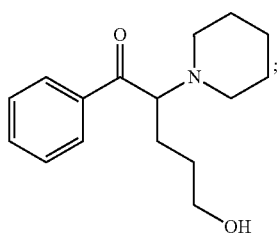 [SMILES: O=C(c1ccccc1)C(CCCO)N1CCCCC1]

or (B) (i) $R^1$ is 1-methylpiperidin-2-yl,
 (ii) $R^2$, $R^3$, $R^4$, $R^5$, and $R^6$ are hydrogen,
 (iii) X is methyl, and the compound is 2-(1-methylpiperidin-2-yl)-1-phenylhexan-1-one:

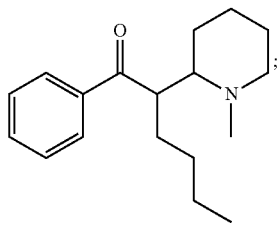 [SMILES: CCCCC(C(=O)c1ccccc1)C1CCCCN1C]

or (C) (i) $R^1$ is 1-methylpiperidin-2-yl,
 (ii) $R^2$, $R^3$, $R^4$, $R^5$, and $R^6$ are hydrogen,
 (iii) X is hydroxy, and the compound is 5-hydroxy-2-(1-methylpiperidin-2-yl)-1-phenylpentan-1-one:

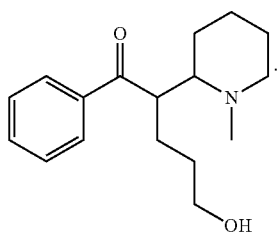 [SMILES: CN1CCCCC1C(CCCO)C(=O)c1ccccc1]

6. The compound of claim 1, wherein $R^1$ is an unsubstituted or substituted azepanyl.

7. The compound of claim 1, wherein—
 (A) (i) $R^1$ is azepan-1-yl,
 (ii) $R^2$, $R^3$, $R^4$, $R^5$, and $R^6$ are hydrogen,
 (iii) X is methyl, and the compound is 2-(azepan-1-yl)-1-phenylhexan-1-one:

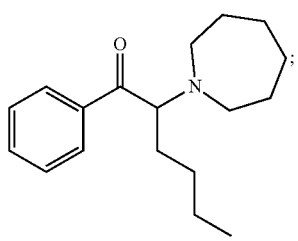 [SMILES: CCCCC(C(=O)c1ccccc1)N1CCCCCC1]

or (B) (i) $R^1$ is azepan-1-yl,
 (ii) $R^2$, $R^3$, $R^4$, $R^5$, and $R^6$ are hydrogen,
 (iii) X is hydroxy, and the compound is 2-(azepan-1-yl)-5-hydroxy-1-phenylpentan-1-one:

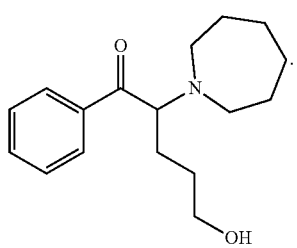 [SMILES: O=C(c1ccccc1)C(CCCO)N1CCCCCC1]

8. The compound of claim 1, wherein $R^1$ is (i) an 8,8-dimethyl-8$\lambda^4$-azabicyclo[3.2.1]octanyl, (ii) a 9-methyl-3-oxa-9-azatricyclo[3.3.1.0$^{2,4}$]nonanyl, or (iii) a 9,9-dimethyl-3-oxa-W-azatricyclo[3.3.1.0$^{2,4}$]nonanyl.

9. A pharmaceutical formulation comprising the compound of claim 1.

10. A method of treating a patient having a disorder linked to the muscarinic acetylcholine receptor, the method comprising:
 administering to the patient a therapeutically effective amount of the pharmaceutical formulation of claim 9.

11. The compound of claim 1, wherein—
 (i) $R^1$ is 8-methyl-8-azabicyclo[3.2.1]octan-3-yl,
 (ii) $R^2$, $R^3$, $R^4$, $R^5$, and $R^6$ are hydrogen,
 (iii) X is hydroxy, and the compound is 5-hydroxy-2-(8-methyl-8-azabicyclo[3.2.1]octan-3-yl)-1-phenylpentan-1-one:

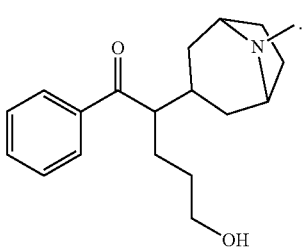 [SMILES: CN1C2CCC1CC(C(CCCO)C(=O)c1ccccc1)C2]

12. The compound of claim 1, wherein the compound of formula (I), formula (II), or formula (III) is the following structure or a salt thereof:

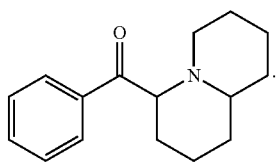 [SMILES: O=C(c1ccccc1)C1CCCC2CCCCN21]

13. The compound of claim 1, wherein the compound of formula (I), formula (II), or formula (III) is the following structure or a salt thereof:

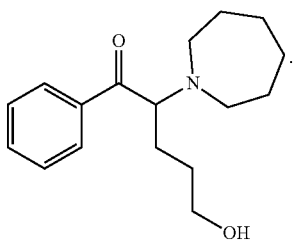 [SMILES: O=C(c1ccccc1)C(CCCO)N1CCCCCC1]

14. The compound of claim 1, wherein the compound of formula (I), formula (II), or formula (III) is the following structure or a salt thereof:

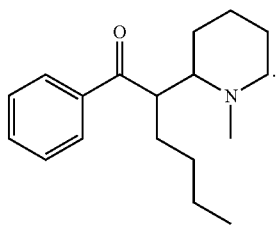 [SMILES: CCCCC(C(=O)c1ccccc1)C1CCCCN1C]

15. The compound of claim 1, wherein the compound of formula (I), formula (II), or formula (III) is the following structure or a salt thereof:

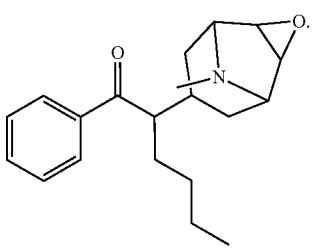 [SMILES: CCCCC(C(=O)c1ccccc1)C1CC2C3OC3C(C1)N2C]

16. The compound of claim 1, wherein the compound of formula (I), formula (II), or formula (III) is the following structure or a salt thereof:

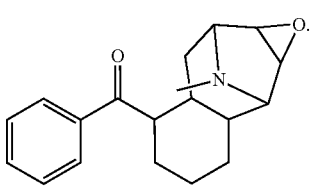 [SMILES: CN1C2CC3C(C(=O)c4ccccc4)CCCC3C1C1OC12]

17. The compound of claim 1, wherein $R^1$ is the 8-methyl-8-azabicyclo[3.2.1]octanyl.

18. The compound of claim 1, wherein the nitrogen atom is a quaternary nitrogen atom.

19. The compound of claim 1, wherein the compound of formula (I), formula (II), or formula (III) is the following structure or a salt thereof:

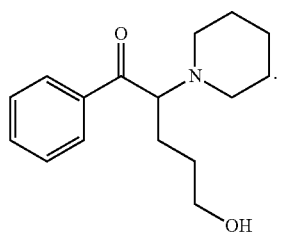 [SMILES: O=C(c1ccccc1)C(CCCO)N1CCCCC1]

20. The compound of claim 1, wherein the compound of formula (I), formula (II), or formula (III) is the following structure or a salt thereof:

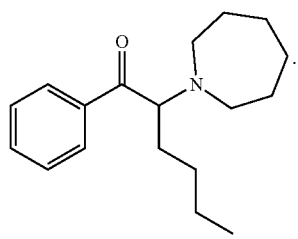 [SMILES: CCCCC(C(=O)c1ccccc1)N1CCCCCC1]

21. The compound of claim 1, wherein the compound of formula (I), formula (II), or formula (III) is the following structure or a salt thereof:

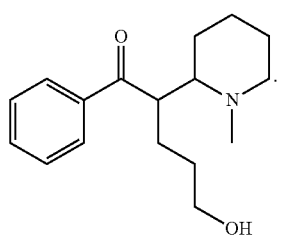 [SMILES: CN1CCCCC1C(CCCO)C(=O)c1ccccc1]

22. The compound of claim 1, wherein the compound of formula (I), formula (II), or formula (III) is the following structure or a salt thereof:

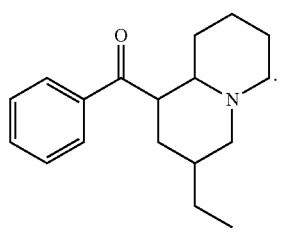 [SMILES: CCC1CC(C(=O)c2ccccc2)C2CCCCN2C1]

23. The compound of claim 1, wherein the compound of formula (I), formula (II), or formula (III) is the following structure or a salt thereof:

24. The compound of claim 1, wherein the compound of formula (I), formula (II), or formula (III) is the following structure or a salt thereof:

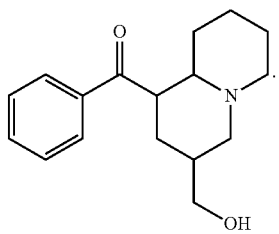

25. The compound of claim 1, wherein the compound of formula (I), formula (II), or formula (III) is the following structure or a salt thereof:

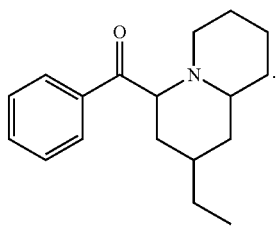 [SMILES: CCC1CC2CCCCN2C(C(=O)c2ccccc2)C1]

26. The compound of claim 1, wherein the compound of formula (I), formula (II), or formula (III) is the following structure or a salt thereof:

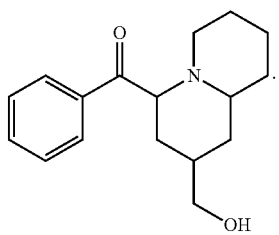 [SMILES: O=C(c1ccccc1)C1CC(CO)CC2CCCCN21]

27. The compound of claim 1, wherein the compound of formula (I), formula (II), or formula (III) is the following structure or a salt thereof:

28. The compound of claim 1, wherein the compound of formula (I), formula (II), or formula (III) is the following structure or a salt thereof:

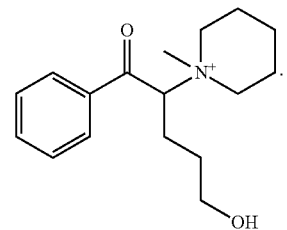 [SMILES: C[N+]1(C(CCCO)C(=O)c2ccccc2)CCCCC1]

29. The compound of claim 1, wherein the compound of formula (I), formula (II), or formula (III) is the following structure or a salt thereof:

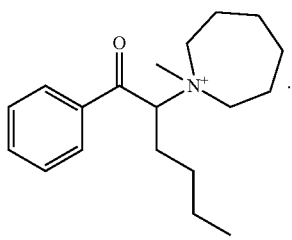 [SMILES: CCCCC(C(=O)c1ccccc1)[N+]1(C)CCCCCC1]

30. The compound of claim 1, wherein the compound of formula (I), formula (II), or formula (III) is the following structure or a salt thereof:

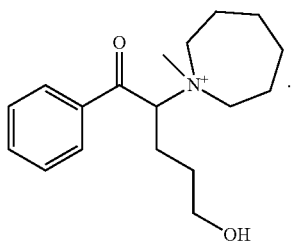 [SMILES: C[N+]1(C(CCCO)C(=O)c2ccccc2)CCCCCC1]

31. The compound of claim 1, wherein the compound of formula (I), formula (II), or formula (III) is the following structure or a salt thereof:

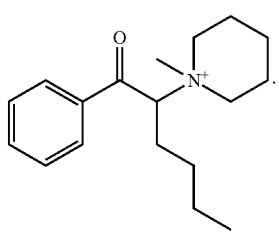

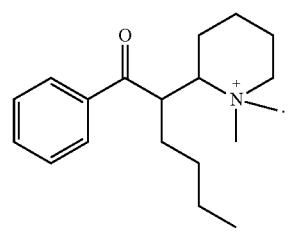

32. The compound of claim 1, wherein the compound of formula (I), formula (II), or formula (III) is the following structure or a salt thereof:

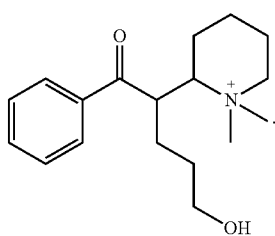

33. The compound of claim 1, wherein the compound of formula (I), formula (II), or formula (III) is the following structure or a salt thereof:

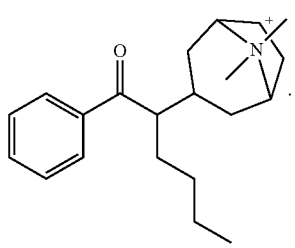

34. The compound of claim 1, wherein the compound of formula (I), formula (II), or formula (III) is the following structure or a salt thereof:

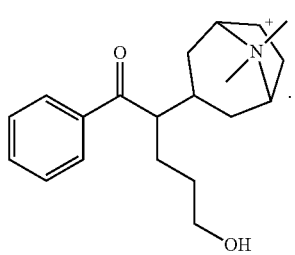

35. The compound of claim 1, wherein the compound of formula (I), formula (II), or formula (III) is the following structure or a salt thereof:

36. The compound of claim 1, wherein the compound of formula (I), formula (II), or formula (III) is the following structure or a salt thereof:

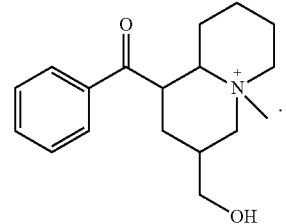

37. The compound of claim 1, wherein the compound of formula (I), formula (II), or formula (III) is the following structure or a salt thereof:

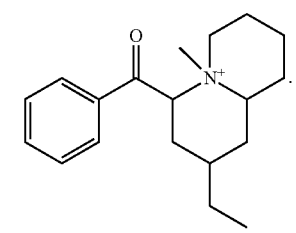 [SMILES: CCC1CC2CCCC[N+]2(C)C(C(=O)c2ccccc2)C1]

38. The compound of claim 1, wherein the compound of formula (I), formula (II), or formula (III) is the following structure or a salt thereof:

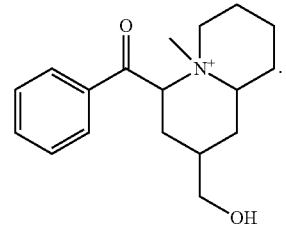 [SMILES: C[N+]12CCCCC1CC(CO)CC2C(=O)c1ccccc1]

39. The compound of claim 1, wherein the compound of formula (I), formula (II), or formula (III) is the following structure or a salt thereof:

40. The compound of claim 1, wherein the compound of formula (I), formula (II), or formula (III) is the following structure or a salt thereof:

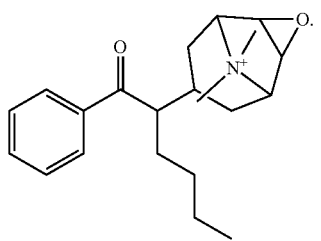 [SMILES: CCCCC(C(=O)c1ccccc1)C1CC2C3OC3C(C1)[N+]2(C)C]

41. The compound of claim 1, wherein the compound of formula (I), formula (II), or formula (III) is the following structure or a salt thereof:

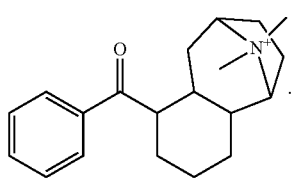 [SMILES: C[N+]1(C)C2CCC1C1CCCC(C(=O)c3ccccc3)C1C2]

42. The compound of claim 1, wherein the compound of formula (I), formula (II), or formula (III) is the following structure or a salt thereof:

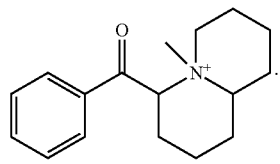 [SMILES: C[N+]12CCCCC1CCCC2C(=O)c1ccccc1]

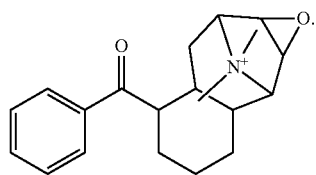

* * * * *